United States Patent
Sapio et al.

(10) Patent No.: US 12,268,610 B2
(45) Date of Patent: Apr. 8, 2025

(54) STEMLESS METAPHYSEAL HUMERAL IMPLANT

(71) Applicant: Howmedica Osteonics Corp., Mahwah, NJ (US)

(72) Inventors: Daniel E. Sapio, Mohegan Lake, NY (US); Ashish Mehta, Rajasthan (IN); Andrew J. Nelson, New City, NY (US); Bernhard Hofstaetter, Munich (DE); Sunny Shorabh, Ghaziabad (IN)

(73) Assignee: Howmedica Osteonics Corp., Mahwah, NJ (US)

( * ) Notice: Subject to any disclaimer, the term of this patent is extended or adjusted under 35 U.S.C. 154(b) by 9 days.

(21) Appl. No.: 17/308,107

(22) Filed: May 5, 2021

(65) Prior Publication Data

US 2021/0346166 A1    Nov. 11, 2021

Related U.S. Application Data

(60) Provisional application No. 63/021,377, filed on May 7, 2020.

(51) Int. Cl.
*A61F 2/40* (2006.01)
*A61B 17/17* (2006.01)
*A61F 2/30* (2006.01)

(52) U.S. Cl.
CPC ........ *A61F 2/4003* (2013.01); *A61B 17/1778* (2016.11); *A61F 2/30771* (2013.01); *A61F 2002/30171* (2013.01); *A61F 2002/30879* (2013.01); *A61F 2002/3093* (2013.01)

(58) Field of Classification Search
None
See application file for complete search history.

(56) References Cited

U.S. PATENT DOCUMENTS

| | | | |
|---|---|---|---|
| 4,042,980 A | 8/1977 | Swanson et al. |
| 4,310,931 A | 1/1982 | Muller |
| 4,550,450 A | 11/1985 | Kinnett |
| 4,714,478 A | 12/1987 | Fischer |
| 4,904,263 A | 2/1990 | Buechel et al. |

(Continued)

FOREIGN PATENT DOCUMENTS

| | | |
|---|---|---|
| CA | 3107922 A1 | 1/2020 |
| CA | 3114808 A1 | 4/2020 |

(Continued)

OTHER PUBLICATIONS

Extended European Search Report issued in Appln. No. 21172289.7 mailed Nov. 15, 2021 (3 pages).

(Continued)

*Primary Examiner* — Ann Schillinger
(74) *Attorney, Agent, or Firm* — Lerner David LLP

(57) ABSTRACT

A stemless prosthetic shoulder joint may include a prosthetic humeral head and a stemless base. The stemless base may include a collar and an anchor extending from the collar intended to anchor the base into the proximal humerus. The base may include a proximal collar having a proximal surface and a bone-engaging surface opposite the proximal surface. The collar may have a superior portion and an inferior portion, the superior portion defining an arc shape and the inferior portion defining a substantially triangular shape.

21 Claims, 17 Drawing Sheets

(56) References Cited

U.S. PATENT DOCUMENTS

| | | | |
|---|---|---|---|
| 4,934,352 A | 6/1990 | Sullivan, Jr. | |
| 4,946,461 A | 8/1990 | Fischer | |
| 4,969,888 A | 11/1990 | Scholten et al. | |
| 5,108,404 A | 4/1992 | Scholten et al. | |
| 5,271,737 A | 12/1993 | Baldwin et al. | |
| 5,314,479 A | 5/1994 | Rockwood, Jr. et al. | |
| 5,330,536 A | 7/1994 | Tager et al. | |
| 5,358,526 A | 10/1994 | Tornier | |
| 5,437,677 A | 8/1995 | Shearer et al. | |
| 5,683,466 A | 11/1997 | Vitale | |
| 5,800,551 A * | 9/1998 | Williamson | A61B 17/1778 623/19.11 |
| 5,910,171 A | 6/1999 | Kummer et al. | |
| 5,944,757 A | 8/1999 | Grammont | |
| 6,187,012 B1 | 2/2001 | Masini | |
| 6,197,062 B1 | 3/2001 | Fenlin | |
| 6,197,063 B1 | 3/2001 | Dews | |
| 6,364,910 B1 * | 4/2002 | Shultz | A61B 17/1684 606/86 R |
| 6,368,353 B1 | 4/2002 | Arcand | |
| 6,436,147 B1 | 8/2002 | Zweymuller | |
| 6,530,957 B1 | 3/2003 | Jack | |
| 6,626,946 B1 | 9/2003 | Walch et al. | |
| 6,673,114 B2 | 1/2004 | Hartdegen et al. | |
| 6,676,705 B1 | 1/2004 | Wolf | |
| 6,679,916 B1 | 1/2004 | Frankle et al. | |
| 6,719,799 B1 | 4/2004 | Kropf | |
| 6,736,851 B2 | 5/2004 | Maroney et al. | |
| 6,749,637 B1 | 6/2004 | Bahler | |
| 6,770,100 B2 | 8/2004 | Draenert | |
| 6,783,549 B1 * | 8/2004 | Stone | A61B 17/1684 623/18.11 |
| 6,783,553 B2 | 8/2004 | Grimes | |
| 6,899,736 B1 * | 5/2005 | Rauscher | A61F 2/40 623/19.12 |
| 6,942,699 B2 | 9/2005 | Stone et al. | |
| 6,953,478 B2 | 10/2005 | Bouttens et al. | |
| 7,169,184 B2 | 1/2007 | Dalla Pria | |
| 7,175,663 B1 | 2/2007 | Stone | |
| 7,189,261 B2 | 3/2007 | Dews et al. | |
| 7,338,498 B2 | 3/2008 | Long et al. | |
| 7,431,736 B2 | 10/2008 | Maroney et al. | |
| 7,517,364 B2 | 4/2009 | Long et al. | |
| 7,572,295 B2 | 8/2009 | Steinberg | |
| 7,585,327 B2 | 9/2009 | Winslow | |
| 7,608,109 B2 | 10/2009 | Dalla Pria | |
| 7,621,961 B2 | 11/2009 | Stone | |
| 7,648,530 B2 | 1/2010 | Habermeyer et al. | |
| 7,670,382 B2 | 3/2010 | Parrott et al. | |
| 7,753,959 B2 | 7/2010 | Berelsman et al. | |
| 7,758,650 B2 | 7/2010 | Dews et al. | |
| 7,819,923 B2 | 10/2010 | Stone et al. | |
| 7,854,767 B2 | 12/2010 | May et al. | |
| 7,867,236 B2 | 1/2011 | Hodorek et al. | |
| 7,867,280 B2 | 1/2011 | Goble et al. | |
| 7,901,408 B2 | 3/2011 | Ek et al. | |
| 7,909,882 B2 | 3/2011 | Stinnette | |
| 8,043,382 B2 | 10/2011 | Kumar et al. | |
| 8,052,758 B1 | 11/2011 | Winslow | |
| 8,062,376 B2 | 11/2011 | Shultz et al. | |
| 8,070,820 B2 | 12/2011 | Winslow et al. | |
| 8,097,040 B2 | 1/2012 | Russo et al. | |
| 8,105,327 B2 | 1/2012 | Long et al. | |
| 8,157,870 B2 | 4/2012 | Kropf et al. | |
| 8,182,541 B2 | 5/2012 | Long et al. | |
| 8,236,059 B2 | 8/2012 | Stone et al. | |
| 8,236,060 B2 | 8/2012 | Justin et al. | |
| 8,246,687 B2 * | 8/2012 | Katrana | A61F 2/4059 623/19.13 |
| 8,277,512 B2 | 10/2012 | Parrott et al. | |
| 8,317,871 B2 | 11/2012 | Stone et al. | |
| 8,388,683 B2 | 3/2013 | Hassler et al. | |
| 8,425,614 B2 | 4/2013 | Winslow et al. | |
| 8,444,646 B2 | 5/2013 | Long et al. | |
| 8,454,703 B2 | 6/2013 | Linares | |
| 8,506,638 B2 | 8/2013 | Vanasse et al. | |
| 8,512,410 B2 | 8/2013 | Metcalfe et al. | |
| 8,540,737 B2 | 9/2013 | Chudik | |
| 8,545,506 B2 | 10/2013 | Long et al. | |
| 8,556,902 B2 | 10/2013 | Ek et al. | |
| 8,591,592 B2 | 11/2013 | Dreyfuss | |
| 8,636,801 B2 | 1/2014 | Hassler et al. | |
| 8,647,387 B2 | 2/2014 | Winslow | |
| 8,663,334 B2 | 3/2014 | Viscardi et al. | |
| 8,690,952 B2 | 4/2014 | Dallmann | |
| 8,690,958 B2 | 4/2014 | Klawitter et al. | |
| 8,702,800 B2 | 4/2014 | Linares et al. | |
| 8,702,804 B2 | 4/2014 | Smith et al. | |
| 8,734,457 B2 | 5/2014 | Bailey et al. | |
| 8,734,491 B2 | 5/2014 | Seavey | |
| 8,753,402 B2 | 6/2014 | Winslow et al. | |
| 8,771,362 B2 | 7/2014 | Isch et al. | |
| 8,790,345 B2 | 7/2014 | Anderson | |
| 8,795,379 B2 | 8/2014 | Smith et al. | |
| 8,814,943 B2 | 8/2014 | Long et al. | |
| 8,814,946 B2 | 8/2014 | Steinberg | |
| 8,840,671 B2 | 9/2014 | Ambacher | |
| 8,843,229 B2 | 9/2014 | Vanasse et al. | |
| 8,845,742 B2 | 9/2014 | Kusogullari et al. | |
| 8,858,641 B2 | 10/2014 | Viscardi et al. | |
| 8,864,834 B2 | 10/2014 | Boileau et al. | |
| 8,870,963 B2 | 10/2014 | Gonzalez-Hernandez | |
| 8,876,900 B2 | 11/2014 | Guederian et al. | |
| 8,876,908 B2 | 11/2014 | Katrana et al. | |
| 8,882,776 B2 | 11/2014 | Long et al. | |
| 8,884,618 B2 | 11/2014 | Mahfouz | |
| 8,906,103 B2 | 12/2014 | Stone et al. | |
| 8,920,508 B2 | 12/2014 | Iannotti et al. | |
| 8,932,663 B2 | 1/2015 | Ritz et al. | |
| 8,936,645 B1 | 1/2015 | Masson | |
| 8,936,646 B2 | 1/2015 | Parrott et al. | |
| 8,968,409 B2 | 3/2015 | Chavarria et al. | |
| 8,968,415 B2 | 3/2015 | Meridew et al. | |
| 8,974,537 B2 | 3/2015 | Dreyfuss | |
| 8,989,460 B2 | 3/2015 | Mahfouz | |
| 8,992,623 B2 | 3/2015 | Hopkins et al. | |
| 9,066,805 B2 | 6/2015 | Berchoux et al. | |
| 9,107,758 B2 | 8/2015 | Long et al. | |
| 9,161,843 B2 | 10/2015 | Deffenbaugh et al. | |
| 9,192,476 B2 | 11/2015 | Thomas et al. | |
| D745,678 S * | 12/2015 | Courtney | D24/155 |
| 9,241,802 B2 | 1/2016 | Klawitter et al. | |
| 9,241,803 B2 | 1/2016 | Stone et al. | |
| 9,271,772 B2 | 3/2016 | Gonzalez-Hernandez | |
| 9,283,083 B2 | 3/2016 | Winslow et al. | |
| 9,289,304 B1 | 3/2016 | Kaufmann | |
| 9,289,306 B2 | 3/2016 | Goldberg et al. | |
| 9,314,344 B2 | 4/2016 | Parrott et al. | |
| 9,320,619 B2 | 4/2016 | Anthony et al. | |
| 9,326,862 B2 | 5/2016 | Smith et al. | |
| 9,326,865 B2 | 5/2016 | Katrana et al. | |
| 9,351,834 B2 | 5/2016 | McDaniel et al. | |
| 9,364,333 B1 | 6/2016 | Paulos | |
| 9,364,334 B2 | 6/2016 | Katrana et al. | |
| 9,408,704 B2 | 8/2016 | Metzger | |
| 9,414,927 B2 | 8/2016 | Iannotti et al. | |
| 9,439,768 B2 | 9/2016 | Iannotti et al. | |
| 9,445,910 B2 | 9/2016 | Chudik | |
| 9,445,911 B2 | 9/2016 | Long et al. | |
| 9,486,320 B2 | 11/2016 | Sharkey | |
| 9,498,344 B2 | 11/2016 | Hodorek et al. | |
| 9,504,581 B2 | 11/2016 | Parrott et al. | |
| 9,510,951 B2 | 12/2016 | Bachmaier | |
| 9,512,445 B2 | 12/2016 | Iannotti | |
| 9,561,109 B2 | 2/2017 | Chavarria et al. | |
| 9,566,162 B2 | 2/2017 | Isch | |
| 9,585,769 B2 | 3/2017 | Lubensky et al. | |
| 9,636,237 B2 * | 5/2017 | Anthony | A61B 17/32053 |
| 9,668,873 B2 * | 6/2017 | Winslow | A61F 2/4081 |
| 9,675,461 B2 | 6/2017 | Mahfouz | |
| 9,693,880 B2 | 6/2017 | Olson et al. | |
| 9,700,436 B2 | 6/2017 | Olson et al. | |
| 9,700,437 B2 | 7/2017 | Anthony et al. | |

(56) References Cited

U.S. PATENT DOCUMENTS

| | | |
|---|---|---|
| 9,713,540 B2 | 7/2017 | Anthony et al. |
| 9,730,797 B2 | 8/2017 | Gonzalez-Hernandez |
| 9,757,240 B2 | 9/2017 | Gonzalez-Hernandez |
| 9,814,587 B2 | 11/2017 | Goldberg et al. |
| 9,820,859 B2 * | 11/2017 | Gervasi ................. A61F 2/4003 |
| 9,849,000 B2 | 12/2017 | Long et al. |
| 9,877,757 B2 | 1/2018 | Berchoux et al. |
| 9,895,230 B2 | 2/2018 | Mahfouz |
| 9,925,048 B2 | 3/2018 | Winslow et al. |
| 9,937,046 B2 | 4/2018 | Mahfouz |
| 9,943,419 B2 | 4/2018 | Anthony et al. |
| 9,956,083 B2 | 5/2018 | Humphrey |
| 9,962,261 B1 | 5/2018 | Scheker |
| 9,962,266 B2 | 5/2018 | Humphrey |
| 9,968,459 B2 | 5/2018 | Chudik |
| 9,974,658 B2 | 5/2018 | Chudik |
| 9,993,341 B2 | 6/2018 | Vanasse et al. |
| 10,016,288 B2 | 7/2018 | McElhaney, Jr. |
| 10,022,229 B2 | 7/2018 | Cappelletti |
| 10,022,237 B2 | 7/2018 | Inares |
| 10,034,758 B2 | 7/2018 | Winslow et al. |
| 10,034,777 B2 | 7/2018 | Poncet et al. |
| 10,039,556 B2 | 8/2018 | Burt |
| 10,052,206 B2 | 8/2018 | Mahfouz |
| 10,064,734 B2 | 9/2018 | Burkhead, Jr. et al. |
| 10,070,960 B2 | 9/2018 | Mahfouz |
| 10,070,967 B2 | 9/2018 | Chavarria et al. |
| 10,076,377 B2 | 9/2018 | Bonutti et al. |
| 10,085,856 B2 | 10/2018 | Anthony et al. |
| 10,166,032 B2 | 1/2019 | Stone et al. |
| 10,172,714 B2 | 1/2019 | Hatzidakis et al. |
| 10,188,522 B2 | 1/2019 | Gonzalez-Hernandez |
| 10,213,243 B2 * | 2/2019 | Courtney, Jr. ..... A61B 17/1637 |
| 10,213,308 B2 | 2/2019 | Scheker |
| 10,213,311 B2 | 2/2019 | Mahfouz |
| 10,226,349 B2 | 3/2019 | Sperling et al. |
| 10,251,755 B2 | 4/2019 | Boileau et al. |
| 10,265,185 B2 | 4/2019 | Goldberg et al. |
| 10,299,939 B2 | 5/2019 | Gonzalez-Hernandez |
| 10,350,071 B2 | 7/2019 | Lerf et al. |
| 10,368,998 B2 | 8/2019 | Chavarria et al. |
| 10,368,999 B2 | 8/2019 | Greiwe |
| 10,390,972 B2 | 8/2019 | Rao |
| 10,413,416 B2 | 9/2019 | Boileau et al. |
| 10,433,969 B2 | 10/2019 | Humphrey |
| 10,449,054 B2 | 10/2019 | Hopkins |
| 10,456,264 B2 | 10/2019 | Hodorek et al. |
| 10,463,499 B2 | 11/2019 | Emerick et al. |
| 10,478,308 B2 | 11/2019 | Habermeyer |
| 10,517,742 B2 | 12/2019 | Long et al. |
| 10,524,919 B2 | 1/2020 | Gonzalez-Hernandez |
| 10,524,931 B2 | 1/2020 | Lubensky et al. |
| 10,588,752 B2 | 3/2020 | Winslow et al. |
| 10,595,886 B2 | 3/2020 | Termanini |
| 10,610,367 B2 | 4/2020 | Humphrey |
| 10,624,748 B2 | 4/2020 | Ek et al. |
| 10,631,992 B2 | 4/2020 | Hopkins |
| 10,632,000 B2 | 4/2020 | Anthony et al. |
| 10,675,154 B2 | 6/2020 | Petraglio et al. |
| 10,722,373 B2 * | 7/2020 | Hodorek ................ A61F 2/4059 |
| 10,751,190 B2 | 8/2020 | Humphrey |
| 10,765,524 B2 | 9/2020 | Boileau et al. |
| 10,765,534 B2 | 9/2020 | McElhaney, Jr. |
| 10,779,951 B2 * | 9/2020 | Kemp .................... A61F 2/4014 |
| 10,792,162 B2 | 10/2020 | Johannaber et al. |
| 10,799,371 B2 | 10/2020 | Anthony et al. |
| 10,813,768 B2 | 10/2020 | Iannotti |
| 10,828,169 B2 | 11/2020 | Britton et al. |
| 10,842,650 B2 | 11/2020 | Poncet et al. |
| 10,849,762 B1 * | 12/2020 | Hodorek ................ A61F 2/4059 |
| 10,898,348 B2 | 1/2021 | Vivanz et al. |
| 10,925,738 B2 | 2/2021 | Winslow et al. |
| 10,925,744 B2 | 2/2021 | Goldberg et al. |
| 10,959,761 B2 | 3/2021 | Dekel et al. |
| 10,987,226 B2 | 4/2021 | Ball |
| 11,197,764 B2 | 12/2021 | Mutchler et al. |
| 11,389,300 B2 * | 7/2022 | Emerick ................. A61B 17/86 |
| 11,857,427 B2 * | 1/2024 | Hodorek ............. A61F 2/30749 |
| 2001/0011193 A1 | 8/2001 | Nogarin |
| 2001/0047210 A1 | 11/2001 | Wolf |
| 2002/0072805 A1 | 6/2002 | Sullivan et al. |
| 2002/0147450 A1 * | 10/2002 | LeHuec ............. A61B 17/1728 |
| | | 606/280 |
| 2002/0156534 A1 | 10/2002 | Grusin et al. |
| 2003/0028253 A1 | 2/2003 | Stone et al. |
| 2003/0078670 A1 | 4/2003 | Grimes |
| 2003/0097183 A1 | 5/2003 | Rauscher et al. |
| 2003/0125810 A1 | 7/2003 | Sullivan et al. |
| 2003/0187510 A1 | 10/2003 | Hyde |
| 2003/0236572 A1 | 12/2003 | Bertram |
| 2004/0064190 A1 | 4/2004 | Ball et al. |
| 2004/0193275 A1 | 9/2004 | Long et al. |
| 2004/0193276 A1 | 9/2004 | Maroney et al. |
| 2004/0193277 A1 | 9/2004 | Long et al. |
| 2004/0193278 A1 | 9/2004 | Maroney et al. |
| 2004/0225367 A1 | 11/2004 | Glien et al. |
| 2005/0033443 A1 | 2/2005 | Blatter et al. |
| 2005/0043805 A1 | 2/2005 | Chudik |
| 2005/0065612 A1 | 3/2005 | Winslow |
| 2005/0071014 A1 | 3/2005 | Barnett et al. |
| 2005/0085915 A1 | 4/2005 | Steinberg |
| 2005/0107882 A1 | 5/2005 | Stone et al. |
| 2005/0143745 A1 | 6/2005 | Hodorek et al. |
| 2005/0278030 A1 | 12/2005 | Tornier et al. |
| 2006/0009774 A1 | 1/2006 | Goble et al. |
| 2006/0009852 A1 | 1/2006 | Winslow et al. |
| 2006/0009853 A1 | 1/2006 | Justin et al. |
| 2006/0020344 A1 | 1/2006 | Shultz et al. |
| 2006/0036328 A1 | 2/2006 | Parrott et al. |
| 2006/0069445 A1 | 3/2006 | Ondrla et al. |
| 2006/0085006 A1 | 4/2006 | Ek et al. |
| 2006/0149390 A1 | 7/2006 | Long et al. |
| 2006/0241775 A1 | 10/2006 | Buss |
| 2007/0005074 A1 | 1/2007 | Chudik |
| 2007/0016304 A1 | 1/2007 | Chudik |
| 2007/0016305 A1 | 1/2007 | Chudik |
| 2007/0027417 A1 | 2/2007 | Chudik |
| 2007/0027477 A1 | 2/2007 | Chudik |
| 2007/0050040 A1 | 3/2007 | Guederian et al. |
| 2007/0100353 A1 | 5/2007 | Chudik |
| 2007/0100447 A1 | 5/2007 | Steinberg |
| 2007/0100458 A1 | 5/2007 | Dalla Pria |
| 2007/0118230 A1 | 5/2007 | Callaway et al. |
| 2007/0123991 A1 | 5/2007 | Steinberg |
| 2007/0142917 A1 | 6/2007 | Roche et al. |
| 2007/0156250 A1 | 7/2007 | Seitz et al. |
| 2007/0162140 A1 | 7/2007 | McDevitt |
| 2007/0162149 A1 | 7/2007 | Kropf et al. |
| 2007/0173945 A1 | 7/2007 | Wiley et al. |
| 2007/0173949 A1 | 7/2007 | Sharps et al. |
| 2007/0179624 A1 | 8/2007 | Stone et al. |
| 2007/0219637 A1 | 9/2007 | Berelsman et al. |
| 2007/0219638 A1 | 9/2007 | Jones et al. |
| 2007/0225821 A1 | 9/2007 | Reubelt et al. |
| 2007/0225822 A1 | 9/2007 | Santilli et al. |
| 2007/0282450 A1 | 12/2007 | Habermeyer et al. |
| 2008/0015691 A1 | 1/2008 | Wyss |
| 2008/0021564 A1 | 1/2008 | Gunther |
| 2008/0065226 A1 | 3/2008 | Long et al. |
| 2008/0177395 A1 | 7/2008 | Stinnette |
| 2008/0183297 A1 | 7/2008 | Boileau et al. |
| 2008/0208353 A1 | 8/2008 | Kumar et al. |
| 2008/0228281 A1 | 9/2008 | Forrer et al. |
| 2008/0306601 A1 | 12/2008 | Dreyfuss |
| 2008/0312749 A1 | 12/2008 | May et al. |
| 2009/0054985 A1 | 2/2009 | Anderson |
| 2009/0062926 A1 | 3/2009 | Wyss |
| 2009/0105838 A1 | 4/2009 | Russo et al. |
| 2009/0143865 A1 | 6/2009 | Hassler et al. |
| 2009/0149961 A1 | 6/2009 | Dallmann |
| 2009/0164021 A1 | 6/2009 | Dallmann |
| 2009/0192622 A1 | 7/2009 | Long et al. |
| 2009/0198238 A1 | 8/2009 | Long et al. |
| 2009/0254188 A1 | 10/2009 | Maroney et al. |

(56) References Cited

U.S. PATENT DOCUMENTS

| | | |
|---|---|---|
| 2009/0259317 A1 | 10/2009 | Steinberg |
| 2009/0265011 A1 | 10/2009 | Mandell |
| 2009/0281630 A1 | 11/2009 | Delince et al. |
| 2009/0287309 A1 | 11/2009 | Walch et al. |
| 2009/0292364 A1 | 11/2009 | Linares |
| 2009/0306782 A1 | 12/2009 | Schwyzer |
| 2010/0049260 A1 | 2/2010 | Long et al. |
| 2010/0070046 A1 | 3/2010 | Steinberg |
| 2010/0076498 A1 | 3/2010 | Tyber et al. |
| 2010/0114326 A1 | 5/2010 | Winslow et al. |
| 2010/0137993 A1 | 6/2010 | Parrott et al. |
| 2010/0185297 A1 | 7/2010 | Steinberg |
| 2010/0191340 A1 | 7/2010 | Dreyfuss |
| 2010/0274360 A1 | 10/2010 | Gunther |
| 2010/0298834 A1 | 11/2010 | Hildebrandt |
| 2011/0035013 A1 | 2/2011 | Winslow et al. |
| 2011/0054624 A1 | 3/2011 | Iannotti |
| 2011/0054631 A1 | 3/2011 | Ratron et al. |
| 2011/0060417 A1 | 3/2011 | Simmen et al. |
| 2011/0130844 A1 | 6/2011 | Ratron et al. |
| 2011/0166661 A1 | 7/2011 | Boileau et al. |
| 2011/0196434 A1 | 8/2011 | Ek et al. |
| 2011/0224673 A1 | 9/2011 | Smith |
| 2011/0304332 A1 | 12/2011 | Mahfouz |
| 2011/0305379 A1 | 12/2011 | Mahfouz |
| 2011/0313533 A1 | 12/2011 | Gunther |
| 2012/0041563 A1 | 2/2012 | Chudik |
| 2012/0101592 A1 | 4/2012 | Thomas et al. |
| 2012/0109321 A1 | 5/2012 | Stone et al. |
| 2012/0109322 A1 | 5/2012 | Gonzalez-Hernandez |
| 2012/0130505 A1 | 5/2012 | Long et al. |
| 2012/0143204 A1 | 6/2012 | Blaylock et al. |
| 2012/0165952 A1 | 6/2012 | Stinnette |
| 2012/0179263 A1 | 7/2012 | Metcalfe et al. |
| 2012/0191202 A1 | 7/2012 | Borowsky |
| 2012/0232666 A1 | 9/2012 | Iannotti |
| 2012/0232667 A1 | 9/2012 | Katrana et al. |
| 2012/0232668 A1 | 9/2012 | Iannotti |
| 2012/0265315 A1 | 10/2012 | Kusogullari et al. |
| 2012/0296435 A1 | 11/2012 | Ambacher |
| 2012/0296436 A1* | 11/2012 | Klawitter ............... A61F 2/4014 623/19.14 |
| 2012/0310360 A1 | 12/2012 | Parrott et al. |
| 2012/0316571 A1 | 12/2012 | Sharkey |
| 2013/0018475 A1 | 1/2013 | Vanasse et al. |
| 2013/0018476 A1* | 1/2013 | Katrana ............... A61F 2/4612 623/19.14 |
| 2013/0053969 A1 | 2/2013 | Linares et al. |
| 2013/0053970 A1 | 2/2013 | Linares et al. |
| 2013/0090736 A1 | 4/2013 | Katrana et al. |
| 2013/0123930 A1 | 5/2013 | Burt |
| 2013/0144394 A1 | 6/2013 | Hassler et al. |
| 2013/0150972 A1 | 6/2013 | Iannotti et al. |
| 2013/0150974 A1 | 6/2013 | Iannotti et al. |
| 2013/0150975 A1 | 6/2013 | Iannotti et al. |
| 2013/0173006 A1 | 7/2013 | Duport |
| 2013/0173007 A1 | 7/2013 | Duport |
| 2013/0178943 A1 | 7/2013 | Duport |
| 2013/0190881 A1 | 7/2013 | Winslow et al. |
| 2013/0190882 A1 | 7/2013 | Humphrey |
| 2013/0197652 A1 | 8/2013 | Ekelund et al. |
| 2013/0211539 A1 | 8/2013 | McDaniel et al. |
| 2013/0245776 A1 | 9/2013 | Long et al. |
| 2013/0261629 A1 | 10/2013 | Anthony et al. |
| 2013/0261754 A1 | 10/2013 | Anthony et al. |
| 2013/0261755 A1 | 10/2013 | Anthony et al. |
| 2013/0282015 A1 | 10/2013 | Lubensky et al. |
| 2013/0304226 A1 | 11/2013 | Ritz et al. |
| 2013/0325130 A1 | 12/2013 | Viscardi et al. |
| 2013/0325133 A1 | 12/2013 | Viscardi et al. |
| 2013/0338780 A1 | 12/2013 | Berchoux et al. |
| 2013/0345817 A1 | 12/2013 | Long et al. |
| 2014/0005789 A1 | 1/2014 | Chavarria et al. |
| 2014/0025173 A1 | 1/2014 | Cardon et al. |
| 2014/0025181 A1 | 1/2014 | Vanasse et al. |
| 2014/0031946 A1 | 1/2014 | Katrana et al. |
| 2014/0107792 A1 | 4/2014 | Hopkins et al. |
| 2014/0121709 A1 | 5/2014 | Gonzalez-Hernandez |
| 2014/0121779 A1 | 5/2014 | Gonzalez-Hernandez |
| 2014/0188231 A1 | 7/2014 | Poncet et al. |
| 2014/0188244 A1 | 7/2014 | Thomas et al. |
| 2014/0222154 A1 | 8/2014 | Klawitter et al. |
| 2014/0228961 A1 | 8/2014 | Linares et al. |
| 2014/0257499 A1* | 9/2014 | Winslow ............... A61F 2/4081 623/19.13 |
| 2014/0277518 A1* | 9/2014 | Iannotti ............... A61F 2/30 623/19.11 |
| 2014/0277521 A1 | 9/2014 | Chavarria et al. |
| 2014/0277522 A1 | 9/2014 | Goldberg et al. |
| 2014/0296988 A1 | 10/2014 | Winslow et al. |
| 2014/0343680 A1 | 11/2014 | Long et al. |
| 2014/0358239 A1 | 12/2014 | Katrana et al. |
| 2014/0358240 A1 | 12/2014 | Katrana et al. |
| 2014/0371863 A1 | 12/2014 | Vanasse et al. |
| 2014/0379089 A1 | 12/2014 | Bachmaier |
| 2015/0012104 A1 | 1/2015 | Boileau et al. |
| 2015/0045898 A1 | 2/2015 | Gonzalez-Hernandez |
| 2015/0066149 A1 | 3/2015 | Parrott et al. |
| 2015/0094819 A1 | 4/2015 | Iannotti et al. |
| 2015/0120031 A1 | 4/2015 | Mahfouz |
| 2015/0127104 A1 | 5/2015 | Levy et al. |
| 2015/0134075 A1 | 5/2015 | Chavarria et al. |
| 2015/0150687 A1 | 6/2015 | Hopkins |
| 2015/0190237 A1 | 7/2015 | Bonin, Jr. et al. |
| 2015/0250601 A1 | 9/2015 | Humphrey |
| 2015/0265411 A1 | 9/2015 | Deransart et al. |
| 2015/0272643 A1 | 10/2015 | Berchoux et al. |
| 2015/0289983 A1 | 10/2015 | Sharkey |
| 2015/0335440 A1 | 11/2015 | Linares et al. |
| 2015/0335441 A1 | 11/2015 | Linares et al. |
| 2015/0342739 A1 | 12/2015 | Mahfouz |
| 2016/0008137 A1 | 1/2016 | Long et al. |
| 2016/0030197 A1 | 2/2016 | Anthony et al. |
| 2016/0038295 A1 | 2/2016 | Anthony et al. |
| 2016/0038296 A1 | 2/2016 | Anthony et al. |
| 2016/0038297 A1 | 2/2016 | Anthony et al. |
| 2016/0038310 A1 | 2/2016 | Anthony et al. |
| 2016/0051367 A1 | 2/2016 | Gervasi et al. |
| 2016/0058561 A1 | 3/2016 | Anthony et al. |
| 2016/0158021 A1 | 6/2016 | Goldberg et al. |
| 2016/0175101 A1 | 6/2016 | Gonzalez-Hernandez |
| 2016/0206436 A1 | 7/2016 | Chavarria et al. |
| 2016/0213474 A9 | 7/2016 | Gonzalez-Hernandez |
| 2016/0213480 A1 | 7/2016 | Stone et al. |
| 2016/0228264 A1 | 8/2016 | Anthony et al. |
| 2016/0242920 A1 | 8/2016 | Parrott et al. |
| 2016/0250030 A1 | 9/2016 | McDaniel et al. |
| 2016/0256287 A1 | 9/2016 | Isch |
| 2016/0262902 A1 | 9/2016 | Winslow et al. |
| 2016/0324648 A1 | 11/2016 | Hodorek et al. |
| 2016/0361173 A1 | 12/2016 | Reubelt et al. |
| 2016/0367374 A1 | 12/2016 | Wecker et al. |
| 2016/0374815 A1 | 12/2016 | Siccardi et al. |
| 2017/0000569 A1 | 1/2017 | Mahfouz |
| 2017/0000613 A1 | 1/2017 | Lerf et al. |
| 2017/0000614 A1 | 1/2017 | Mahfouz |
| 2017/0000615 A1 | 1/2017 | Mahfouz |
| 2017/0020677 A1 | 1/2017 | McElhaney, Jr. |
| 2017/0027701 A1 | 2/2017 | Mahfouz |
| 2017/0042687 A1 | 2/2017 | Boileau et al. |
| 2017/0049573 A1 | 2/2017 | Hodorek et al. |
| 2017/0056187 A1 | 3/2017 | Humphrey et al. |
| 2017/0071748 A1 | 3/2017 | Humphrey |
| 2017/0100251 A1 | 4/2017 | Ek et al. |
| 2017/0105843 A1 | 4/2017 | Britton et al. |
| 2017/0128220 A1 | 5/2017 | Iannotti |
| 2017/0143498 A1 | 5/2017 | Chavarria et al. |
| 2017/0156873 A1 | 6/2017 | Hopkins |
| 2017/0172763 A1 | 6/2017 | Lubensky et al. |
| 2017/0181859 A1 | 6/2017 | Linares |
| 2017/0209196 A1 | 7/2017 | Zajac et al. |
| 2017/0224492 A1 | 8/2017 | Winslow et al. |
| 2017/0273800 A1 | 9/2017 | Emerick et al. |
| 2017/0281355 A1 | 10/2017 | Winslow et al. |

(56) References Cited

U.S. PATENT DOCUMENTS

| | | |
|---|---|---|
| 2017/0281356 A1 | 10/2017 | Goldberg et al. |
| 2017/0304063 A1 | 10/2017 | Hatzidakis et al. |
| 2017/0325971 A1 | 11/2017 | Gonzalez-Hernandez |
| 2017/0340449 A1 | 11/2017 | Deransart et al. |
| 2018/0000600 A1 | 1/2018 | Gonzalez-Hernandez |
| 2018/0064547 A1 | 3/2018 | Greiwe |
| 2018/0085226 A1 | 3/2018 | Baumgarten |
| 2018/0104073 A1 | 4/2018 | Long et al. |
| 2018/0161168 A1 | 6/2018 | Johannaber et al. |
| 2018/0161176 A1 | 6/2018 | Vivanz et al. |
| 2018/0168814 A1 | 6/2018 | Scheker |
| 2018/0193150 A1 | 7/2018 | Winslow et al. |
| 2018/0199967 A1 | 7/2018 | Russo et al. |
| 2018/0214276 A1 | 8/2018 | Humphrey |
| 2018/0250138 A1 | 9/2018 | Alidousti et al. |
| 2018/0256217 A1 | 9/2018 | Dekel et al. |
| 2018/0256341 A1 | 9/2018 | Vanasse et al. |
| 2018/0271667 A1 | 9/2018 | Kemp et al. |
| 2018/0271668 A1 | 9/2018 | Kemp et al. |
| 2018/0280151 A1 | 10/2018 | Humphrey |
| 2018/0280152 A1 | 10/2018 | Mutchler et al. |
| 2018/0296355 A1 | 10/2018 | Petraglio et al. |
| 2018/0296366 A1 | 10/2018 | McElhaney |
| 2018/0311053 A9 | 11/2018 | Anthony et al. |
| 2018/0344486 A1 | 12/2018 | Poncet et al. |
| 2018/0368859 A1 | 12/2018 | Burt |
| 2018/0368982 A1 | 12/2018 | Ball |
| 2019/0015213 A1 | 1/2019 | Mahfouz |
| 2019/0015222 A1 | 1/2019 | Anthony et al. |
| 2019/0046326 A1 | 2/2019 | Ball |
| 2019/0105167 A1 | 4/2019 | Hatzidakis et al. |
| 2019/0105168 A1 | 4/2019 | Habermeyer |
| 2019/0105169 A1 | 4/2019 | Sperling |
| 2019/0133790 A1 | 5/2019 | Viscardi et al. |
| 2019/0151097 A1 | 5/2019 | Lerf et al. |
| 2019/0151105 A1 | 5/2019 | Gonzalez-Hernandez |
| 2019/0159906 A1 | 5/2019 | Knox et al. |
| 2019/0175354 A1 | 6/2019 | Knox et al. |
| 2019/0192305 A1 | 6/2019 | Frankle et al. |
| 2019/0231543 A1 | 8/2019 | Goldberg et al. |
| 2019/0231544 A1 | 8/2019 | Boileau et al. |
| 2019/0269423 A1 | 9/2019 | Termanini |
| 2019/0274835 A1 | 9/2019 | Wiley et al. |
| 2019/0274847 A1 | 9/2019 | Gonzalez-Hernandez |
| 2019/0350719 A1 | 11/2019 | Greiwe |
| 2019/0358045 A1 | 11/2019 | Boileau et al. |
| 2020/0000600 A1 | 1/2020 | Hopkins |
| 2020/0008947 A1 | 1/2020 | Emerick et al. |
| 2020/0085593 A1 | 3/2020 | Long et al. |
| 2020/0121466 A1 | 4/2020 | Gonzalez-Hernandez |
| 2020/0121467 A1 | 4/2020 | Hodorek et al. |
| 2020/0129300 A1 | 4/2020 | Sanchez-Sotelo et al. |
| 2020/0138585 A1 | 5/2020 | Tepic |
| 2020/0146834 A1 | 5/2020 | Hodorek et al. |
| 2020/0188123 A1 * | 6/2020 | Hodorek ............. A61F 2/30749 |
| 2020/0214845 A1 | 7/2020 | Knox et al. |
| 2020/0222199 A1 | 7/2020 | Hopkins |
| 2020/0253749 A1 | 8/2020 | Anthony et al. |
| 2020/0281727 A1 | 9/2020 | Dang et al. |
| 2020/0289277 A1 | 9/2020 | Lefebvre et al. |
| 2020/0315807 A1 | 10/2020 | Hatzidakis et al. |
| 2020/0352728 A1 | 11/2020 | Hodorek et al. |
| 2020/0368033 A1 | 11/2020 | Britton et al. |
| 2020/0368039 A1 | 11/2020 | McElhaney, Jr. |
| 2020/0383796 A1 | 12/2020 | Johannaber et al. |
| 2021/0007856 A1 | 1/2021 | Nelson et al. |
| 2021/0022878 A1 | 1/2021 | Boileau et al. |
| 2021/0030550 A1 | 2/2021 | Ek et al. |
| 2021/0038394 A1 | 2/2021 | Winslow et al. |
| 2021/0038400 A1 | 2/2021 | Iannotti |
| 2021/0045887 A1 | 2/2021 | Wagner et al. |
| 2021/0045895 A1 | 2/2021 | Sapio et al. |
| 2021/0077263 A1 | 3/2021 | Hodorek et al. |
| 2021/0077278 A1 | 3/2021 | Poncet et al. |
| 2021/0228372 A1 | 7/2021 | Knox et al. |

FOREIGN PATENT DOCUMENTS

| | | | |
|---|---|---|---|
| DE | 102008010478 A1 | 8/2009 | |
| EP | 1402854 A2 | 3/2004 | |
| EP | 1415621 A2 | 5/2004 | |
| EP | 1782765 A1 | 5/2007 | |
| EP | 2564814 A1 * | 3/2013 | ........... A61F 2/4003 |
| EP | 2604225 A1 | 6/2013 | |
| EP | 2604227 A1 | 6/2013 | |
| EP | 2965720 A1 | 1/2016 | |
| FR | 2652498 A1 | 4/1991 | |
| FR | 2773469 A1 | 7/1999 | |
| FR | 3023471 A1 | 1/2016 | |
| WO | 9309733 A1 | 5/1993 | |
| WO | 9617553 A1 | 6/1996 | |
| WO | 2003005933 A2 | 1/2003 | |
| WO | 2008000928 A2 | 1/2008 | |
| WO | 2013064569 A1 | 5/2013 | |
| WO | 2014067961 A1 | 5/2014 | |
| WO | 2018183484 A1 | 10/2018 | |
| WO | 2019079104 A2 | 4/2019 | |
| WO | WO-2019106278 A1 * | 6/2019 | ........... A61F 2/4003 |
| WO | 2020072465 A2 | 4/2020 | |

OTHER PUBLICATIONS

Comprehensive Nano Stemless Shoulder Anatomic and Reverse, Surgical Technique, Biomet Orthopedics, 60 pages, 2012.
Extended European Search Report for EP Application No. 18163008, dated Jul. 12, 2018.
Extended European Search Report for Application No. 19207145.4, dated Feb. 18, 2020, pp. 1-4.
FibuLock Nail, Ankle Fracture System, Surgical Technique, Sonoma Orthopedic Products, Inc, 2015, pp. 1-28.
Sapio et al., U.S. Appl. No. 60/021,377, filed May 7, 2020, titled "Stemless Metaphyseal Humeral Implant".
International Search Report and Written Opinion for PCT/US2017/048491 dated Dec. 5, 2017.
Web site: Innomed orthopedic instruments, 'Shoulder instruments', Jul. 1, 2016 <http://www.innomed.net/shoulder_rets_standard.htm> Accessed Mar. 29, 2018.
Partial Supplementary European Search Report including the Provisional Opinion for Application No. EP 17844446.9 dated Mar. 24, 2020, 15 pages.
Exlended European Search Report for Application No. EP17844446.9 dated Jun. 25, 2020.
International Search Report and Written Opinion for PCT/US2018/024824 dated Jul. 10, 2018. 12 pages.

* cited by examiner

STEMLESS METAPHYSEAL HUMERAL IMPLANT

CROSS-REFERENCE TO RELATED APPLICATIONS

This application claims the benefit of the filing date of U.S. Provisional Patent Application No. 63/021,377 filed May 7, 2020, the disclosure of which is hereby incorporated herein by reference.

FIELD OF THE DISCLOSURE

The present application relates to a shoulder prosthesis, and in particular to a humerus implant.

BACKGROUND OF THE DISCLOSURE

Over time and through repeated use, bones and joints can become damaged or worn. For example, repetitive strain on bones and joints (e.g., through athletic activity), traumatic events, and certain diseases (e.g., arthritis) can cause cartilage in joint areas, for example, which normally provides a cushioning effect, to wear down. When the cartilage wears down, fluid can accumulate in the joint areas, resulting in pain, stiffness, and decreased mobility. The same can happen in cases where tendons in a joint become lax or soft tissues in or adjacent the joint become damaged or worn.

Arthroplasty procedures can be used to repair such damaged joints. During a typical arthroplasty procedure, an arthritic or otherwise dysfunctional joint can be remodeled or realigned. A prosthesis or prostheses can be implanted to repair the damaged region(s). Arthroplasty procedures may take place in any number of different regions of the body, such as the knees, hips, shoulders, or elbows, for example. One type of arthroplasty procedure is a shoulder arthroplasty, in which a damaged shoulder joint may be replaced with prosthetic implants. The shoulder joint may have been damaged by, for example, arthritis (e.g., severe osteoarthritis or degenerative arthritis), trauma, or a rare destructive joint disease.

Prostheses that are implanted into a damaged region may provide support and structure to the damaged region, and may help to restore the damaged region, thereby enhancing its functionality. Prior to implantation of a prosthesis in a damaged region, the damaged region may be prepared to receive the prosthesis. In the case of a shoulder arthroplasty procedure, one or more of the bones in the shoulder area, such as the humerus and/or glenoid, may be treated (e.g., cut, drilled, reamed, and/or resurfaced) to provide one or more surfaces that can align with the implant and thereby accommodate the implant.

It is often preferable to maintain as much of a patient's natural bone stock as possible during such a procedure. Prostheses generally have a certain life expectancy and in certain cases need to be replaced at some point. If one or more prostheses need to be removed and/or replaced in a revision procedure, a large bone void could be left after their removal. In certain cases, this bone void is not ideal for receipt of revision components. Preserving natural bone stock may be desirable for the ability to even perform a revision procedure.

In total or partial arthroplasty surgery, stemmed prostheses are often used which generally include a long stem that passes through a center of a long bone, the stem helping to anchor the remaining components of the prosthesis. However, stemmed prostheses may result in a large amount of healthy bone being removed in order to accommodate the stem. In some cases, stemless prostheses may be used, which may result in less healthy bone stock being removed. However, in some cases, a stemmed prosthesis may offer better anchorage than a stemless prosthesis and a stemless shoulder prosthesis may require the removal of significant proximal humeral bone, which may compromise the proximal humerus bone and result in more challenging revision surgeries.

BRIEF SUMMARY OF THE DISCLOSURE

A first aspect of the present disclosure includes a base member of a stemless shoulder implant, the base member includes a proximal collar having a proximal surface and a bone-engaging surface opposite the proximal surface, the collar having a superior portion and an inferior portion, the superior portion defining an arc shape and the inferior portion defining a substantially triangular shape.

In other embodiments, the base member may include a central anchor extending distally along a longitudinal axis of the base member from the bone-engaging surface of the collar a first distance to a central tip. The central anchor may include a plurality of ribs extending radially outward of the central anchor. The base member may include at least one chisel slot extending from the bone-engaging surface to the proximal surface adjacent a portion of the central anchor, the at least one chisel slot configured to receive a tool for removing bone. The base may include a plurality of peripheral supports each positioned radially outwardly of the central anchor and extending distally from the bone-engaging surface of the collar. Each peripheral support may extend a second distance to a peripheral tip, the first distance being greater than the second distance. The plurality of ribs of the anchor may extend along the central anchor and connects to a respective one of the plurality of peripheral supports. The plurality of ribs of the anchor may connect to an inner surface of the respective one of the peripheral supports. The arc of the superior portion of the collar may extend between a first peripheral support and a second peripheral support of the plurality of peripheral supports. The base member may include four peripheral supports. At least one chisel slot may extend from the bone-engaging surface to the proximal surface adjacent a portion of the central anchor, the at least one chisel slot configured to receive a tool for removing bone. The base member may include four chisel slots. At least a portion of the collar may include an enhanced fixation surface for promoting bone ingrowth. The triangular shape of the inferior portion is defined by a first side edge extending along a first line and a second side edge extending along a second line, an angle defined between the first line and the second line may be from about 60 degrees to about 75 degrees. An angle from the central tip of the central anchor to opposing side walls of a respective one of the plurality of supports may be 30 degrees. Each of the plurality of supports may extend along the same diameter of the base component such that each support is an equal distance from a central longitudinal axis of the base. The plurality of supports may include a first inferior support and a second posterior support, an angle between a first central point of the first inferior support and a second central point of the second posterior support may be from about 105 degrees to about 120 degrees.

A base member of a stemless should implant, the base member includes a proximal collar having a proximal surface and a bone-engaging surface opposite the proximal surface, the collar having a superior portion and an inferior portion, a perimeter of the superior portion defining an arc shape and a perimeter of the inferior portion defining a substantially triangular shape, and central anchor extending distally from the bone-engaging surface.

In other embodiments, the base member may include at least one chisel slot extending from the proximal surface to the bone-engaging surface, the at least one chisel slot configured to receive a tool for removing bone. The central anchor may include ribs extending along and radially outward of the central anchor. The base member may include peripheral supports positioned radially outward of the ribs and connected to the ribs. A first chisel slot may define a first shape and a second chisel slot may define a second shape different than the first shape. At least a portion of the collar or the central anchor may include an enhanced fixation surface for bone ingrowth.

DETAILED DESCRIPTION

It should be understood that although the term "stemless implant" is used herein, the term does not indicate that a stemless implant fully lacks any anchor, but rather a stemless implant may include an anchor that is significantly smaller and/or shorter than stems of typical known stemmed implants. Further, the stemless implants of the present disclosure generally include a base member intended for coupling to an end of a first bone of a joint, such as a humerus or femur, and an articulating member intended to attach to the base member and to provide articulation with the second bone of the joint, such as a glenoid or acetabulum (or a corresponding prosthesis attached to the second bone). As used herein, the term "proximal" refers to a location closer to an individual's heart, and the term "distal" refers to a location farther away from the individual's heart. When used in the context of an implant, the terms "proximal" and "distal" refer to locations on the implant closer to, or farther away from, the heart when the implant is implanted in an intended manner. Further, as used herein, anterior refers to a position closer to the front of the body, and posterior refers to a position closer to the rear of the body. Further, with reference to features of the base components discussed throughout the disclosure, the term "height" refers to a distance in the proximal-distal direction, and the term "width" refers to a distance extending in an anterior-posterior direction. Moreover, the term "superior" and "inferior" are relative terms, and superior refers to a location closer to the head, while inferior refers to a location closer to the feet.

Figure 1:
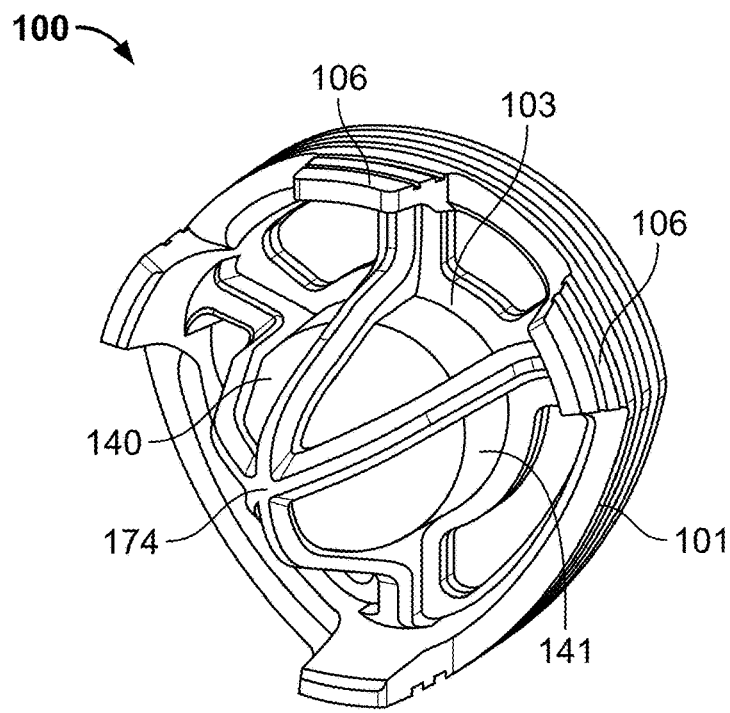
FIG. 1 is a top perspective view of a base of a stemless shoulder implant according to a first aspect of the disclosure.
Figure 2A:
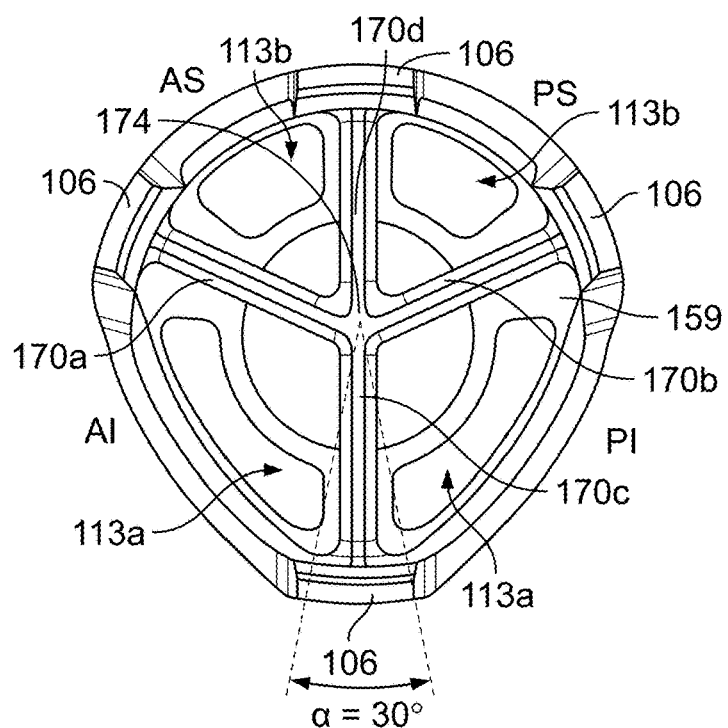
FIGS. 2A and 2B are top views of the base of FIG. 1.
Figure 2B:
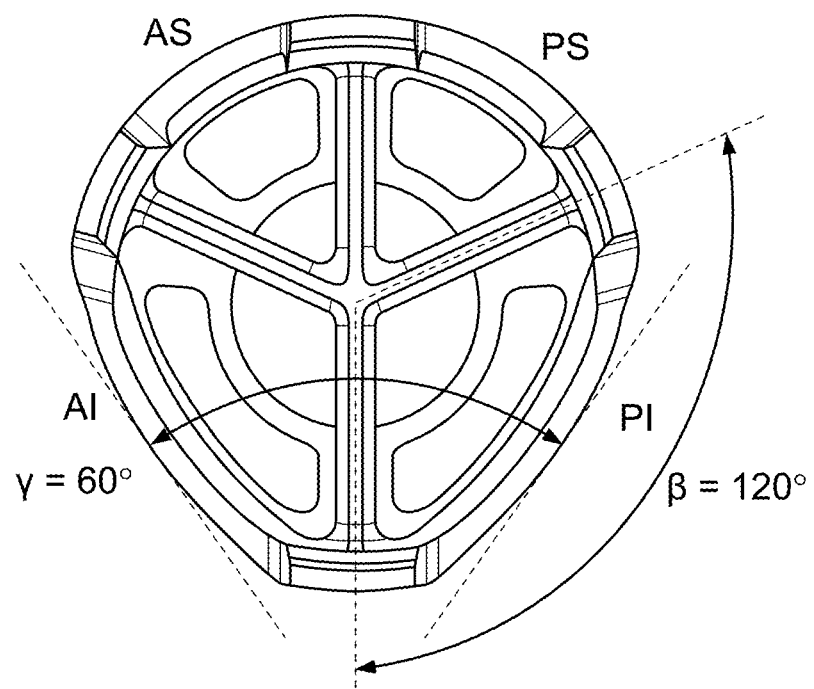
Figure 3:
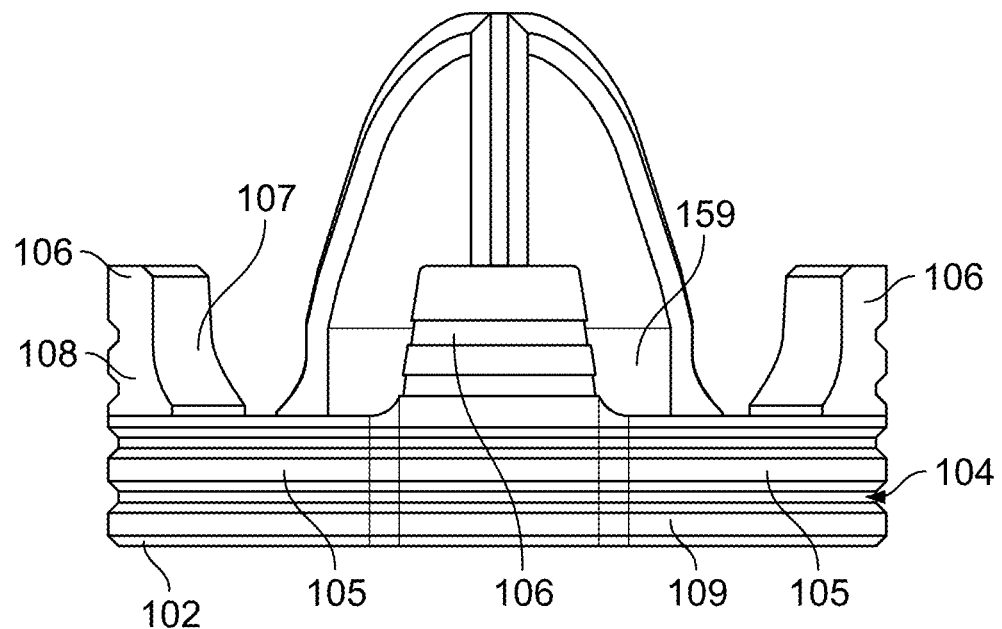
FIG. 3 is a side view of the base of FIG. 1.

FIGS. 1-3 show a base 100 of a stemless implant according to a first aspect of the disclosure. Base 100 generally includes collar 101 and central anchor 140 coupled thereto (or integrally formed therewith). Collar 101 includes a proximal end surface 102, a distal bone-engaging surface 103, and side wall 104 extending along the circumference of the collar and extending distal to bone-engaging surface 103. Side wall 104 includes supports 106 extending distally from side wall 104. Supports 106 are spaced apart from one another around the circumference of the collar 101. In other words, side wall 104 includes supports 106 connected to one another by walled portions 105. Supports 106 extend distally from bone-engaging surface 103 a first distance while walled portions 105 extend distally from bone-engaging surface 103 a second distance less than the first distance. Anchor 140 extends a third distance distally from bone-engaging surface 103, the third distance being greater than each of the first and the second distances. As shown in FIG.

3, supports 106 may each have a concave inner surface 107 which increases surface area which provides for greater fixation. Further, such concavity increases compression to help achieve a press fit between base 100 and the bone which also facilitates greater fixation. Supports 106 may assist in initial fixation of base 100 within the patient. As shown in FIGS. 1 and 3, the outer surface 109 of side wall 104 may include ridges to facilitate bone ingrowth of the implanted base 100. The surface ridges may extend in the circumferential direction on both walled portions 105 and supports 106 of side wall 104. Supports 106 may terminate at side surfaces 108 that include grooves (not shown) along the height of the side surface to enhance both long and short term fixation of the base. In some cases, the grooves may be formed of porous materials to further enhance long term fixation. Additionally, collar 101 may have an arched side profile between keels rather than the flat profile shown.

In another embodiment, the supports 106 may alternatively or additionally include surface ridges that extend vertically on the side wall. In other embodiments, base 100 may include supports 106 only in the superior-inferior direction and not in the anterior-posterior direction. Alternatively, in another embodiment, the base may not include any supports.

Anchor 140 is coupled to collar 101 at a first end 141 and extends distally from the collar 101 along a longitudinal axis to a second end 174. In the illustrated embodiment, anchor 140 is tapered along the longitudinal axis so that first end 141 has a relatively large diameter, with the diameter of the anchor generally narrowing toward second end 174. Anchor 140 has a generally rounded profile in the side view, as shown in FIG. 3. From the top view, shown in FIG. 2, anchor 140 has a substantially circular shape at first end 141. In some examples, it may be appropriate for anchor 140 to be of uniform size throughout and not tapered. Base 100 further includes ribs 170 that connect supports 106 to anchor 140 and extend along anchor 140 to second end 174. In this regard, ribs 170 extend from side wall 104 along bone-engaging surface 103 and along anchor 140 to all meet at second 174 of anchor 140, as shown in FIG. 2. Ribs 170 provide structural support to supports 106 and advantageously facilitate fixation of the base 100 in bone. In the illustrated embodiment, there are four ribs 170 and four supports 106, each rib 170 connecting to a corresponding support 106 at a central portion of the support 106. Ribs 170 define four portions of collar 101, namely, an Anterior-Superior portion (AS), Anterior-Inferior portion (AI), Posterior-Superior portion (PS), and a Posterior-Inferior portion (PI). In other examples, there may be more or fewer supports 106 and ribs 170, and the supports 106 and ribs 170 need not have a one-to-one correspondence.

Base 100 includes one or more enhanced fixation surfaces 159 to allow for greater bone ingrowth into the base 100. Enhanced fixation surface 159 may take the form of a porous metal surface, such as porous titanium alloy, including Tritanium® by Howmedica Osteonics Corporation. Enhanced fixation surface 159 may be positioned on bone-engaging surface 103 and/or a portion of anchor 140. Additionally, enhanced fixation surface 159 may extend on a radially inner surface of side wall 104 Enhanced fixation surface 159 may be rougher than the adjacent surfaces of bone-engaging surface 103 and anchor 140, resulting in greater friction between the enhanced fixation surface 159 and the bone. This increased friction may help provide additional fixation by providing additional resistance against pull-out forces. When implanted, much of the fixation between the bone and the base 100 may initially result from the interaction between the bone and one or more of the anchor 140, the ribs 170, and the supports 106. However, after bone grows into the base 100, including into the enhanced fixation surface 159, much of the fixation between the bone and the base 100 may result from that bone ingrowth.

Base 100 includes chisel slots 113 extending through bone-engaging surface 103 to proximal surface 102. Chisel slots 113 are positioned between side wall 104 and anchor 140 and between adjacent ribs 170 such that in the illustrated embodiment there are four chisel slots 113. Chisel slots 113a are positioned on portions AI and PI of base 100 and each has an elongated "U" shape. Chisel slots 113b are positioned on portions AS and PS and each has a substantially trapezoidal shape. Chisel slots 113 are sized and positioned to facilitate a revision procedure after base 100 has been implanted into a patient for an amount of time. Chisel slots 113 allow a surgeon to insert a tool, such as a bone chisel or reamer, into each slot 113 in order to chisel, ream, or otherwise cut away at bone.

Base 100 is adapted to receive an articulating component (not shown) of the stemless implant. In the illustrated example, base 100 may be adapted to couple to a proximal humerus of a patient, with a prosthetic humeral head adapted to couple to the base. In this regard, base 100 includes opening 123 extending distally into the base from collar 101 for receiving at least a portion of the prosthetic humeral head. The prosthetic humeral head is intended to articulate with a native or prosthetic glenoid of the shoulder joint. The opening may have any shape that suitably mates with the corresponding portion of the prosthetic humeral head, in one example a taper such as a Morse taper may be used to lock the prosthetic humeral head to base 100.

Base 100 advantageously defines collar 101 having a "shield" shape, as shown in FIG. 2 such that a superior portion is generally rounded and an inferior portion is substantially triangular. The shape of collar 101 may resemble an escutcheon, almond, or tear drop shape. Such shapes are defined by a substantially rounded portion at a first end connected to inwardly tapering sides at an opposite end. Such a shape is in contrast to implants of the prior art which are generally round and substantially circular. In this regard, portions AS and PS of collar 101 define a substantially rounded profile, and the collar tapers inward to a central position between portions AI and PI. In the illustrated embodiment, a support 106 is positioned at the central position at which the inward taper of the AI and PI portions intersect. The tapering portions AI/PI of collar 101 may be curved or straight, and in this embodiment are shown as having a slight curve. Although, in other examples, the side wall 104 may not include a support but may rather include a wall having a constant height, and regardless, the AI and PI portions intersect due to the inwardly tapering shape of the inferior portions of the collar.

Ribs 170 include four ribs in the anterior position 170a, posterior position 170b, inferior position 170c, and superior position 170d. The angle β between inferior rib 170c and posterior rib 170b is from about 100 degrees to about 125 degrees, and in this embodiment, as shown in FIG. 2B, is about 120 degrees. The angle α defined by the span of each peripheral support 106 is from about 20 degrees to about 40 degrees, and is shown as about 30 degrees in FIG. 2A. The angle of the taper of the shield, defined as γ in FIG. 2B, is from about 60 degrees to about 80 degrees, and is shown as 60 degrees.

The cancellous bone in the proximal humeral metaphysis has varying density, and increases in density from the center of the resection plane to the outer cortical shell. Such an increase occurs in a ratio of about 1:5 from the center to the cortical shell, with the area between the center and the cortical shell forming a density gradient. With stemless implants, stability of the implant may be based, at least initially, on a press-fit, interference connection between the bone and the implant. The greater the density of the bone, the more press-fit that is induced thereby increasing the stability of the implant. By targeting the high density zones, the implant preferably engages the cancellous bone closest to the cortical shell. However, the implant preferably does not penetrate the cortical shell walls to minimize the risk of fracture of the cortical shell. Accordingly, an advantageous humeral base implant design engages the press-fit zones close to the cortical shell without penetrating it.

Figure 4:
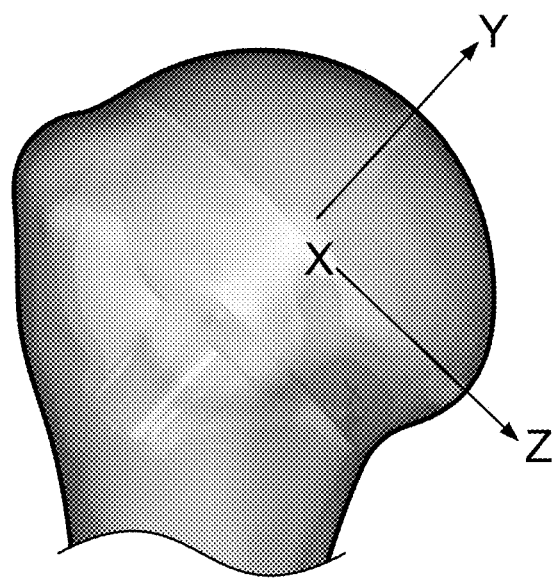
FIG. 4 is a schematic representation of a circular base of a shoulder implant of the prior art implanted within a humerus bone.
Figure 5:
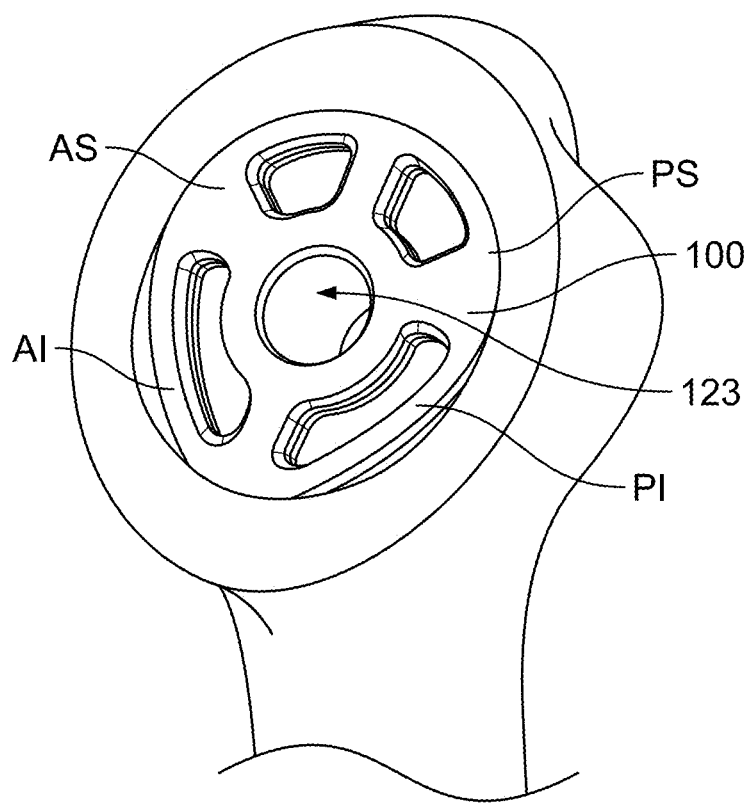
FIG. 5 is a schematic representation of the base of FIG. 1 implanted within a humerus bone.
Figure 6:
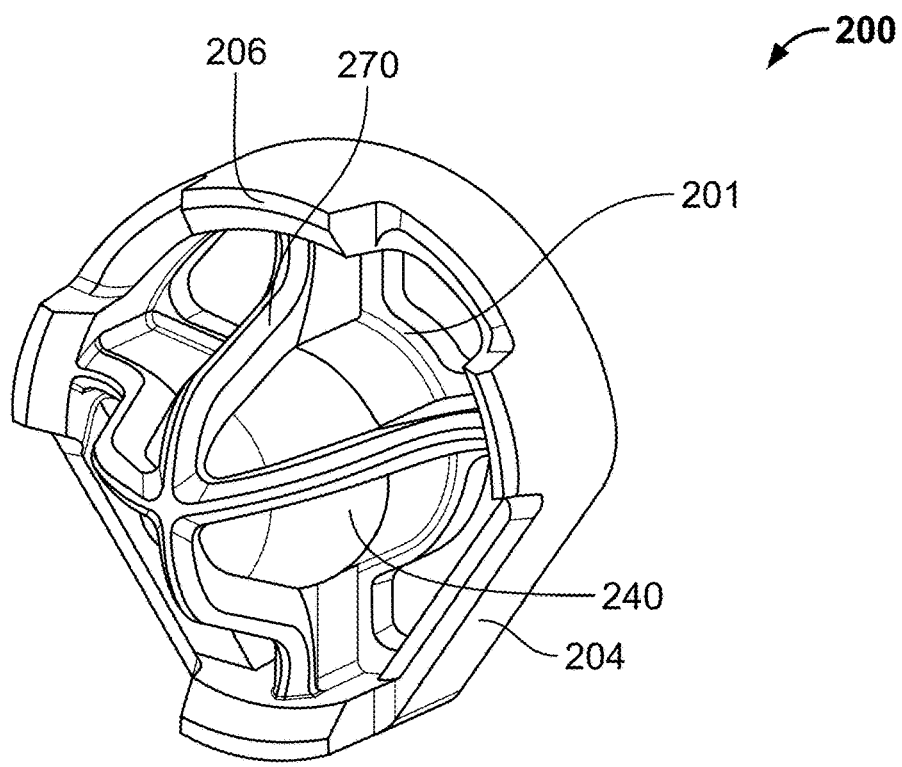
FIG. 6 is a top perspective view of a base of a stemless shoulder implant according to a second aspect of the disclosure.

Prior bases of stemless shoulder implants have been designed with circular profile. The circular bases of the prior art tend to result in high cortical shell penetration rates because the anatomy of the humerus changes in a distal-inferior direction. Such penetration is shown in FIG. 4 in which the round base component penetrates the cortical shell at the location marked with an X. In comparison, with the "shield" shape of the base of the present disclosure, the risk of such penetration and thus fracture is reduced because the shield shape mimics the anatomy of the humerus bone. FIG. 5 shows base 100 implanted within a humerus bone.

This shape advantageously allows for penetration of high density zones including the cancellous bone relatively close to the cortical shell without penetrating into the cortical shell. The rounded superior portions (AS/PS) and tapered inferior portions (AI/PI) allow for targeting the best bone quality to maximize implant stability while simultaneously minimizing risks of cortical shell fracture. Various additional embodiments of a base of a prosthetic stemless shoulder implant are described below. It should be understood that components of some of these embodiments may be combined with components of other embodiments in any suitable fashion.

FIGS. 6-9 show base 200 according to a second aspect of the disclosure. Base 200 is similar to base 100 in many respects, the similar or identical features of which will not be described again here.

Figure 7:
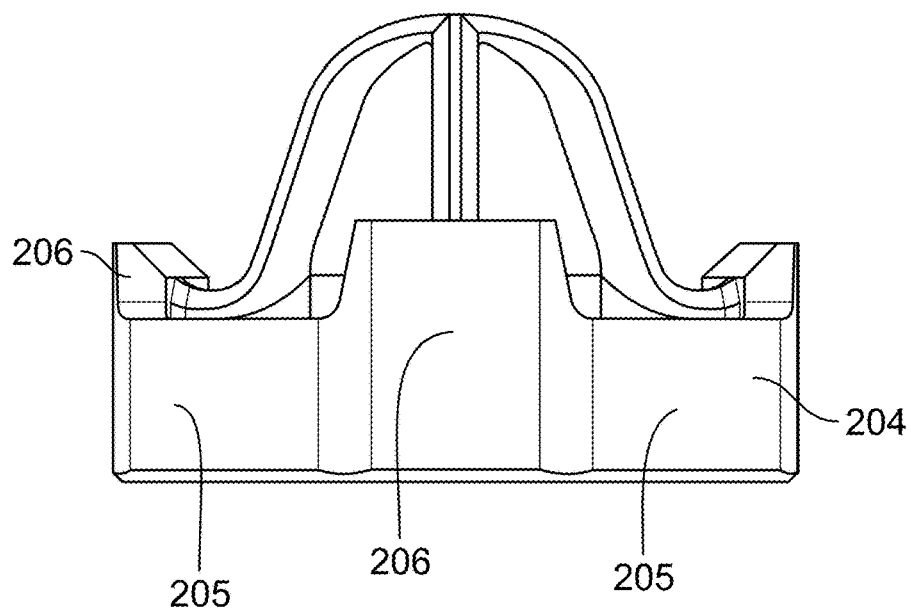
FIG. 7 is a side view of the base of FIG. 6.

Base 200 includes collar 201 and anchor 240 extending distally from the collar. Base 200 further includes ribs 270 substantially similar to ribs 170, except that ribs 270 extend to a greater height. As shown in FIG. 7, side wall 204 includes walled portions 205 connecting supports 206. In this embodiment, walled portions 205 extend further distally than do walled portions 105 of base 100. Additionally, side wall 204 has a smooth surface rather than a ridged surface.

Figure 8:
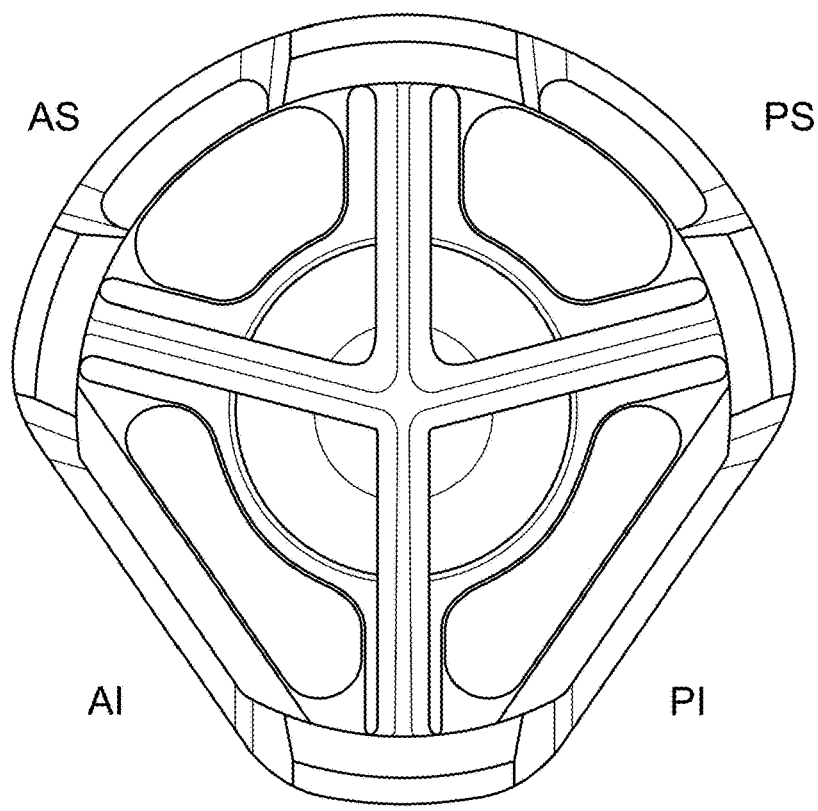
FIG. 8 is a top view of the base of FIG. 6.

As shown in FIG. 8, collar 201 of base 200 includes the shield shape defined by the four portions of the collar, including AS, PS, AI, and PI. The superior portion of the collar, i.e. AS and PS portions, defines a rounded shape which defines an arc of about 170-190 degrees. The inferior portion of the collar, i.e. AI and PI portions of the collar, defines a substantially "V" shape of two intersecting, inwardly tapering sides, although the apex of the "V" shape may be rounded. Despite the tapered shape of base 200, supports 206 may be positioned extending along the same diameter of the base. In other words, each of the supports 206 extend an equal distance from a longitudinal center of the base.

Figure 9:
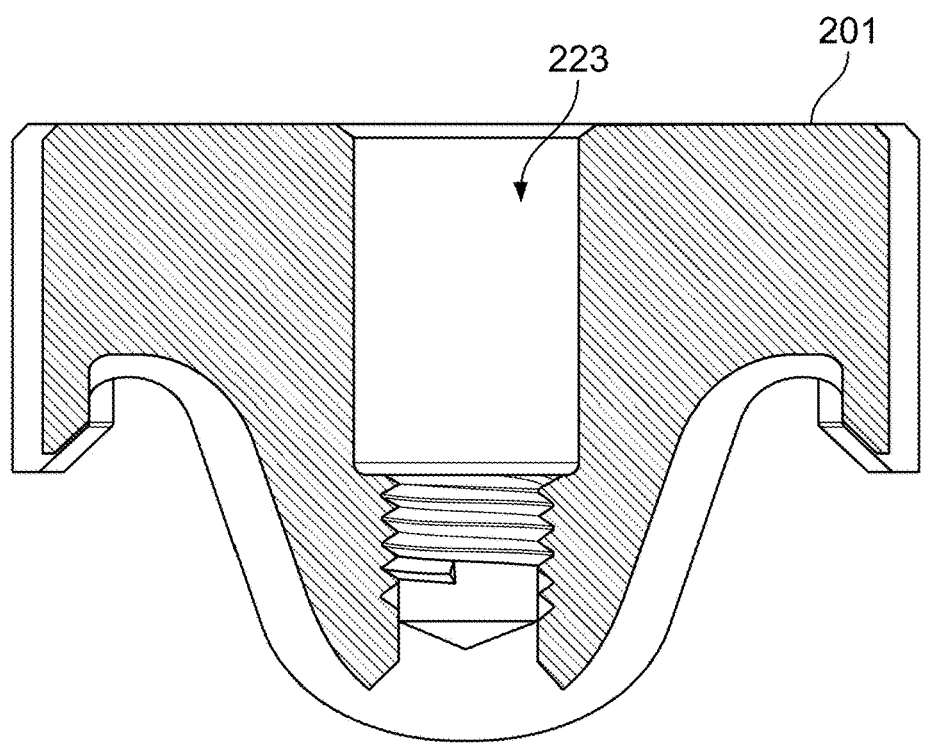
FIG. 9 is a cross-section of the base of FIG. 6.

FIG. 9 shows opening 223 extending into proximal surface 202 distally into base 200. Opening 223 includes threads for threaded engagement with an impaction or extraction tool. Additionally, opening 223 includes Morse taper for engagement with a prosthetic humeral head component to secure the prosthetic humeral head component to the base component.

Figures 10, 11:
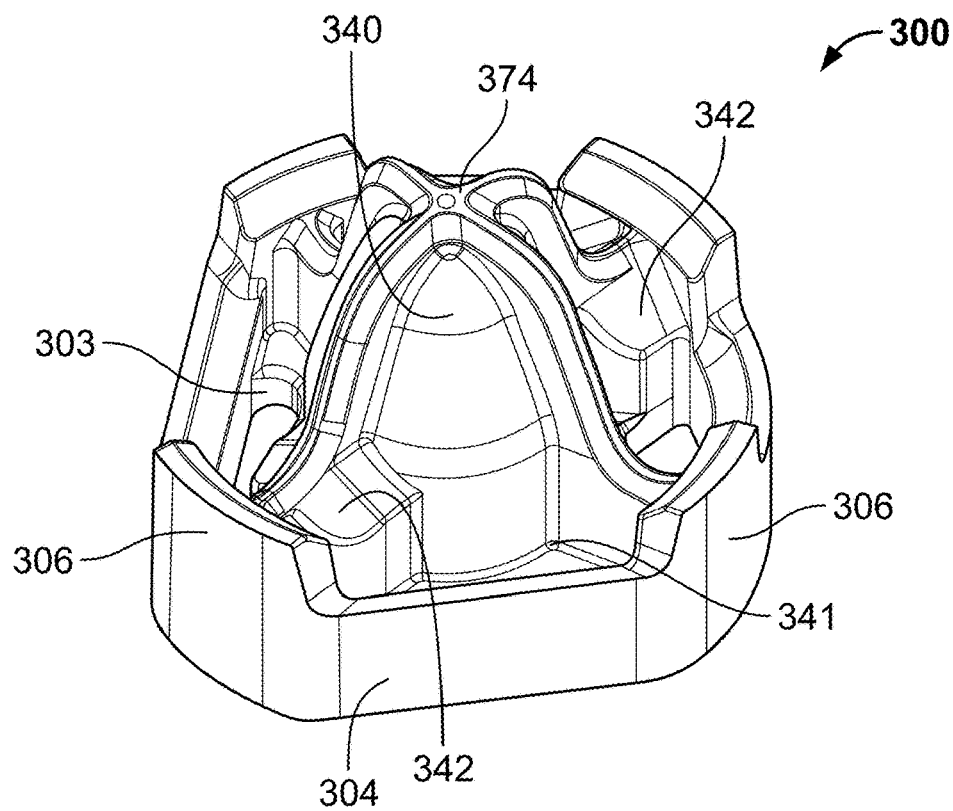
FIG. 10 is a top perspective view of a base of a stemless shoulder implant according to a second aspect of the disclosure.
FIG. 11 is a top view of the base of FIG. 10.
Figure 12:
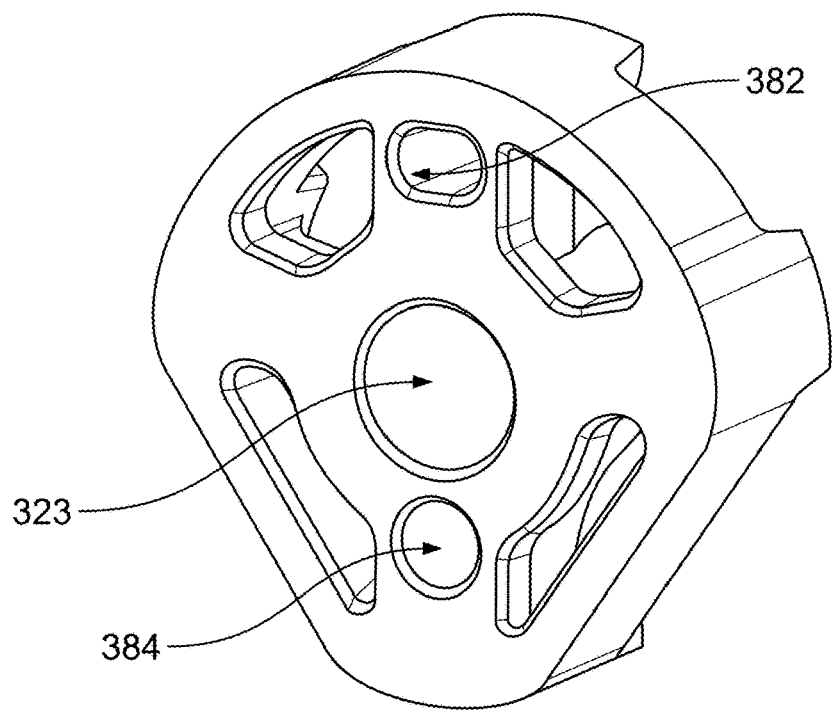
FIG. 12 is a bottom perspective view of the base of FIG. 10.

FIGS. 10-12 show base 300, similar to the prior-described bases in many respects, the similar or identical features of which will not be described again here. As shown in FIG. 10, base 300 includes arms 342 extending distally from bone-engaging surface 303 and connecting first end 341 of anchor 340 to supports 306 of side wall 304 in positions extending superior and inferior to anchor 340. Ribs 370a extend from second end 374 of anchor 340 along arms 342 and connect to supports 306, as shown in the top view in FIG. 11. Arms 342 have a width that is greater than a width of ribs 370, shown in FIG. 11. Ribs 370b extend distally from bone-engaging surface 303 rather than from arms 342 in opposing anterior and posterior sides of anchor 340.

Referring to FIG. 12, base 300 further includes openings 382 and 384 for receiving trial components. In the illustrated embodiment, openings 382 and 384 are positioned on opposing superior, inferior sides of opening 323, respectively. In the illustrated embodiment, opening 382 has an ovular shape while opening 384 has a circular shape. In other examples, openings 382 and 384 may have any shape that facilitates engagement with attachment features of a trial component.

FIGS. 13-16 show base 400 according to another aspect of the present disclosure, which shares many similar features to the previously described bases, the similar features of which will not be described herein.

Base 400 includes ribs 470 extending along anchor 440 and connecting to inner surface 407 of supports 406 of the side wall 404. Each rib 470 has a substantially constant width from its connection at a respective support 406 to its connection to the others of the plurality of ribs 470 at second end 474 of anchor 440. As discussed above in connection with ribs 170 of base 100, similarly ribs 470 provide structural support to supports 406 of side wall 404 and further facilitate fixation of base 400 in bone.

Figure 13:
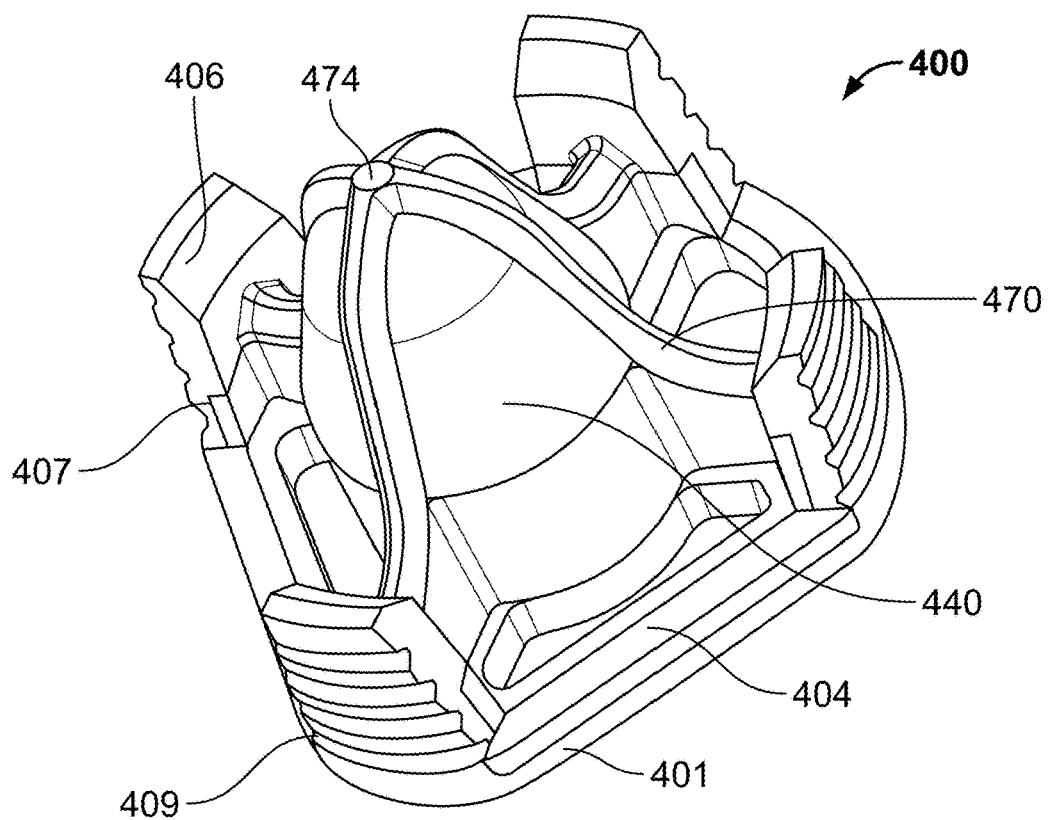
FIG. 13 is a top perspective view of a base of a stemless shoulder implant according to another aspect of the disclosure.
Figure 14:
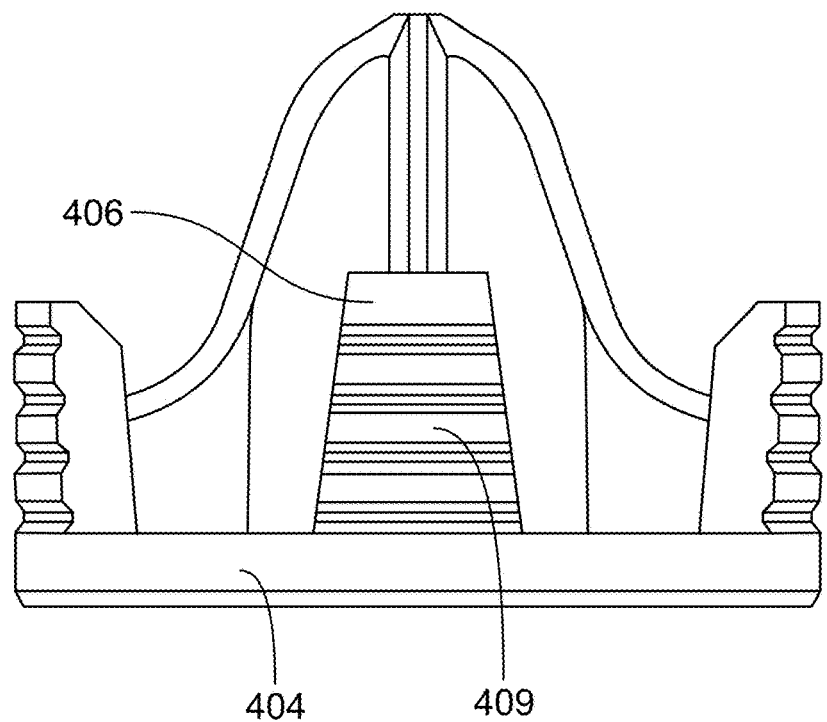
FIG. 14 is a side view of the base of FIG. 13.
Figure 15:
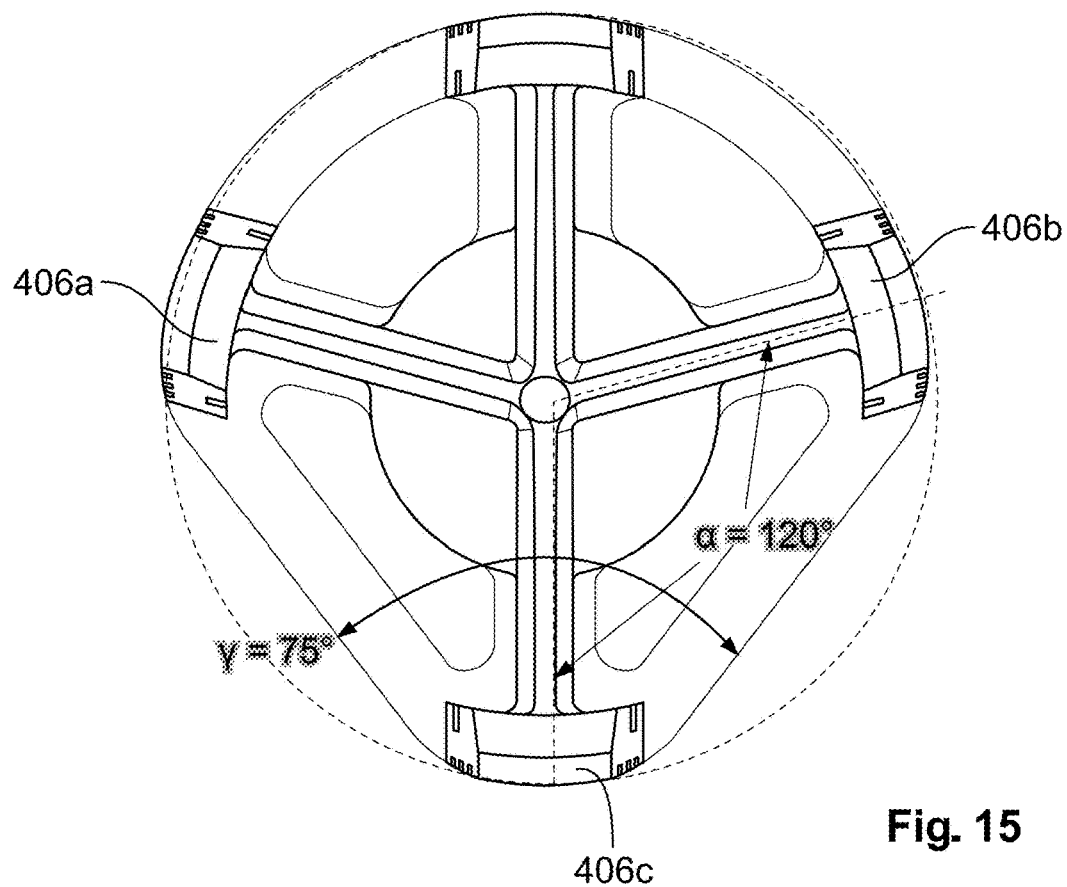
FIG. 15 is a top view of the base of FIG. 13.
Figure 16:
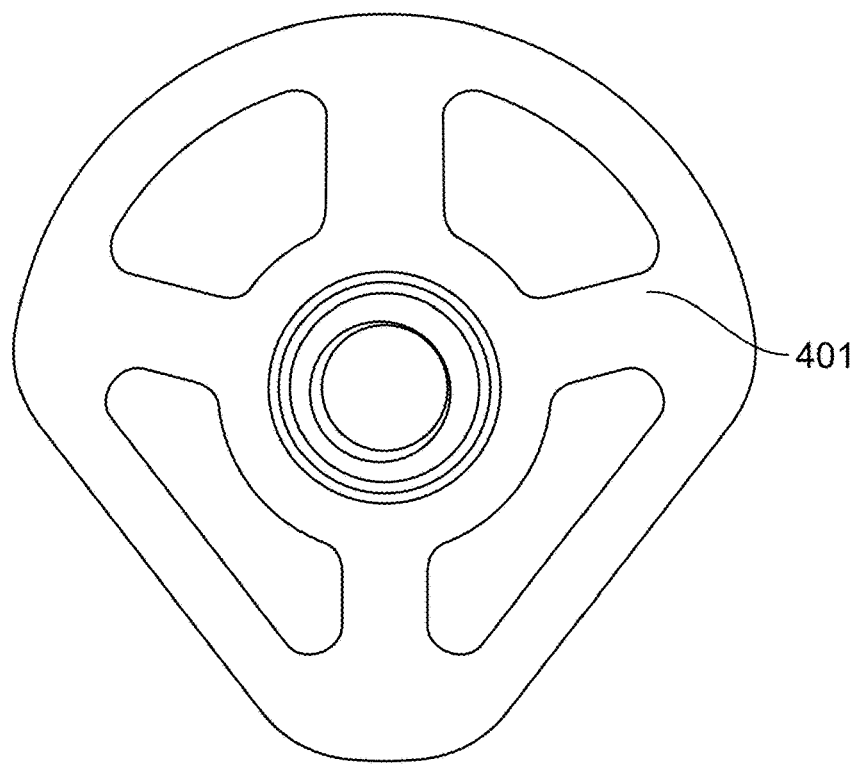
FIG. 16 is a bottom view of the base of FIG. 13.

As best shown in FIGS. 13 and 14, outer surfaces 409 of supports 406 of the side wall 404 include circumferentially extending ridges to facilitate bone ingrowth and frictional stability of the implanted base 400, although in other embodiments the ridges may additionally or alternatively extend vertically. Referring to FIGS. 15 and 16, base 400 has the advantageous "shield" shape described above in which the collar 401 defines a perimeter having a superior portion having an arc shape and an inferior portion that defines a substantially "V" shape connected to opposing ends of the arc. In this example, the V-shape is substantially straight and defines an angle γ that is about 75 degrees, as shown in FIG. 15. Additionally, the angle α, defined between the inferior and posterior ribs 170b, 170c is about 120 degrees. As shown by the broken line around the perimeter of the base, supports 406 lie on the same diameter of the base. In other words, each of the supports 206 extend an equal distance from a longitudinal center of the base. Further, the distal tip as well as the Morse taper for connecting a head component (not shown) aligns with the center of this diameter defined by the supports. In this embodiment, the opposing ends of the arc of the superior portion are defined by supports 406a and 406b and the apex of the "V" is defined by support 406c. Base 400 is symmetric about the superior-inferior plane.

In other examples, the base does not include supports 406 at such locations on collar 401. Rather, side wall 404 of base 400 may maintain the "shield" shape with side wall 404 having a continuous height, defined in the proximal-distal direction.

In methods of use of bases 100-400, the base may be attached to an impactor, such as an impactor disclosed in U.S. Provisional Patent Application No. 62/885,864, entitled "Shoulder Implant Impactor with Stabilization Features," filed on Aug. 13, 2019, the disclosure of which is hereby incorporated by reference herein. The impactor contacts a proximal resected surface of the humerus and the impactor is impacted to move the base at least partially within the humerus. Advantageously, the impactor may have a "shield" shape to mimic the shape of bases 100-400, described herein.

Figure 17:
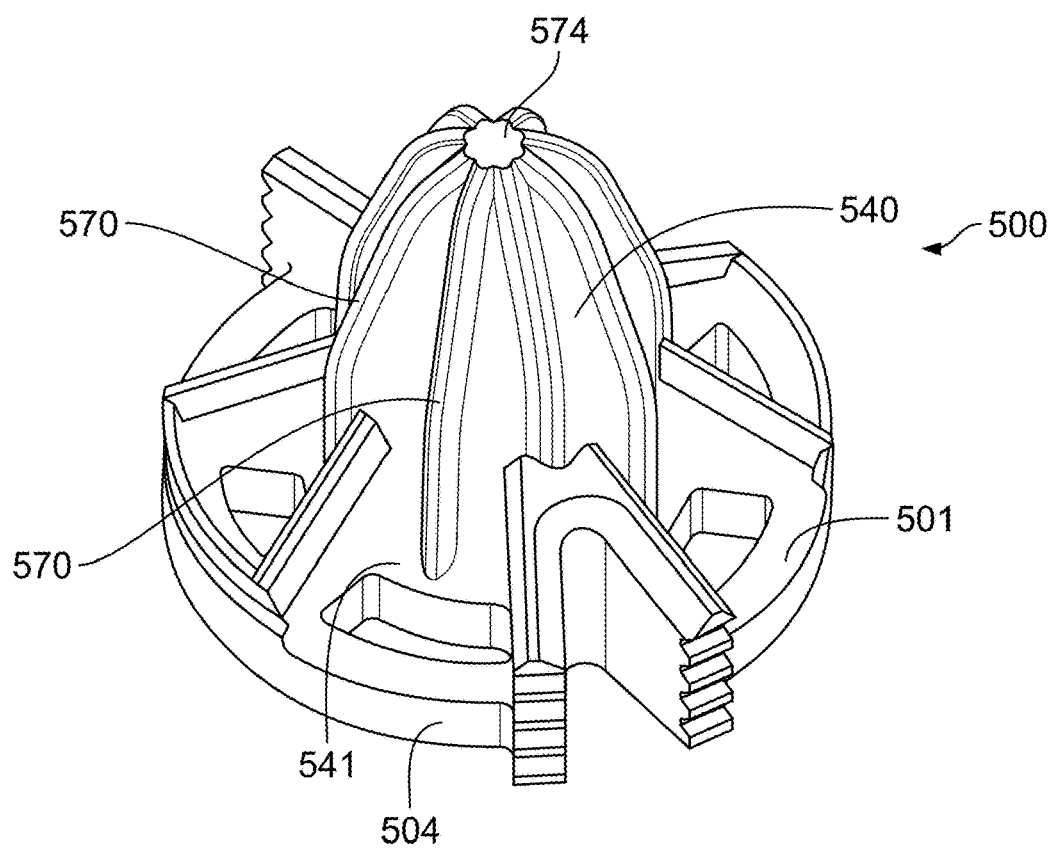
FIG. 17 is a top perspective view of a base of a stemless shoulder implant according to another aspect of the disclosure.
Figure 18:
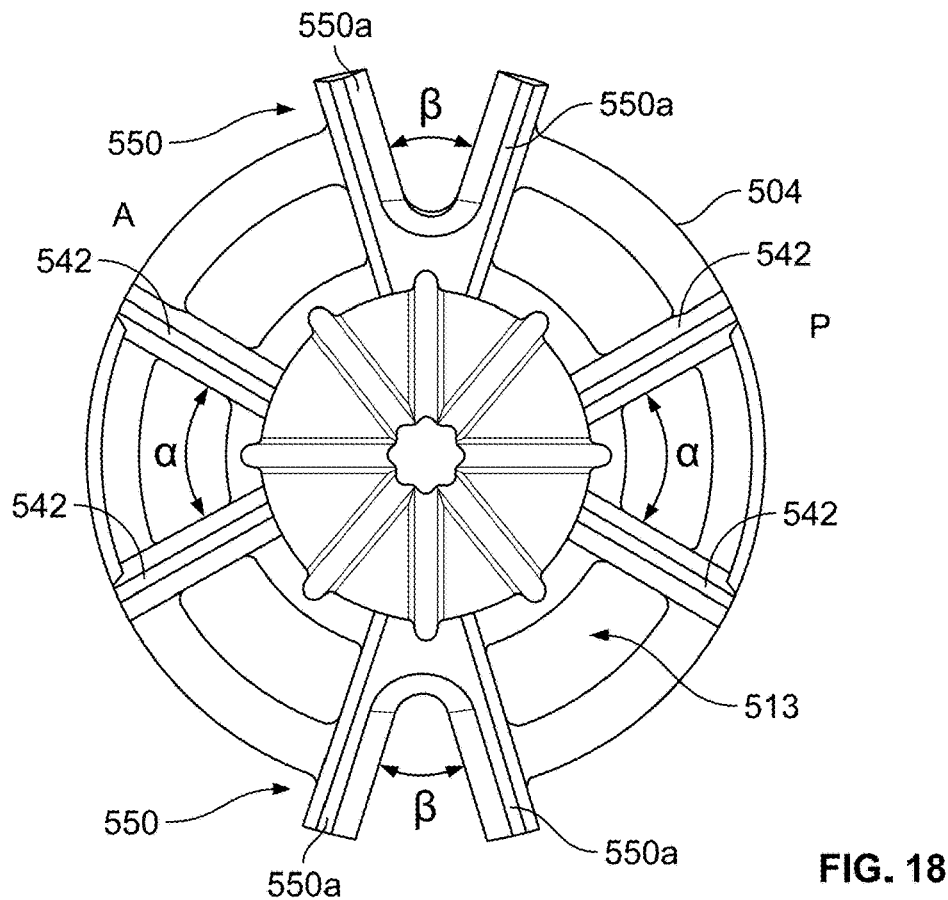
FIG. 18 is a top view of the base of FIG. 17.

FIGS. 17-18 show base 500 according to another aspect of the present disclosure. Base 500 includes similar features to bases 100-400 described above, the similar features of which will not be described herein.

Base 500 includes collar 501 having a substantially circular shape defined by side wall 504. Although, in other examples, the collar may define a "shield" shape as described above. Central anchor 540 extends distally from collar 501 and has a rounded shape which tapers inwardly from first end 541 to second end 574 such that second end 574 has a smaller diameter than first end 541. Anchor 540 includes a plurality of ribs 570 extending from first end 541 to second end 574, each of the plurality of ribs 570 meeting one another at second end 574 of anchor 540. As best shown in FIG. 18, base 500 includes eight ribs 570, although the base may include more or fewer ribs 570 in other examples.

With reference to FIG. 18, base 500 further includes a plurality of arms 542 extending radially outward from anchor 540 to side wall 504. Arms 542 extend distally a first distance from collar 501, and side wall 504 extends distally a second distance that is less than the first distance. From the top view, the plurality of arms 542 include two opposing pairs of adjacent arms, each pair of arms defines an angle α between the two adjacent arms. A first pair of arms 542 is positioned on an anterior side (A) of base 500 and the second pair of arms 542 is positioned on a posterior side (P) of base 500.

Base 500 includes extensions 550 extending radially outward of anchor 540 and defining a "V" shape extending radially beyond side wall 504. In the illustrated embodiment, base 500 includes two extensions 550. A first extension 550 is positioned superiorly to anchor 540 and a second extension 550 is positioned inferiorly to anchor 540. Collar 501 has an open perimeter at extensions 550, and side wall 504 terminates at its connection points with each extension leg 550a. In other words, each pair of legs 550a interrupts the continuity of side wall 504.

To facilitate a revision surgery, base 500 includes chisel slots 513 defining openings through collar 501. Chisel slots 513 are positioned radially outward of anchor 540 and between extensions 550 and arms 542. In the illustrated example, there are six chisel slots 513, each having an elongated substantially "U" shape or rounded trapezoidal arms. In particular, a first pair of chisel slots 513 may be positioned between each pair of arms 542, and four additional chisel slots may be positioned between each circumferentially adjacent arm 542 and arm 550a.

Figure 19:
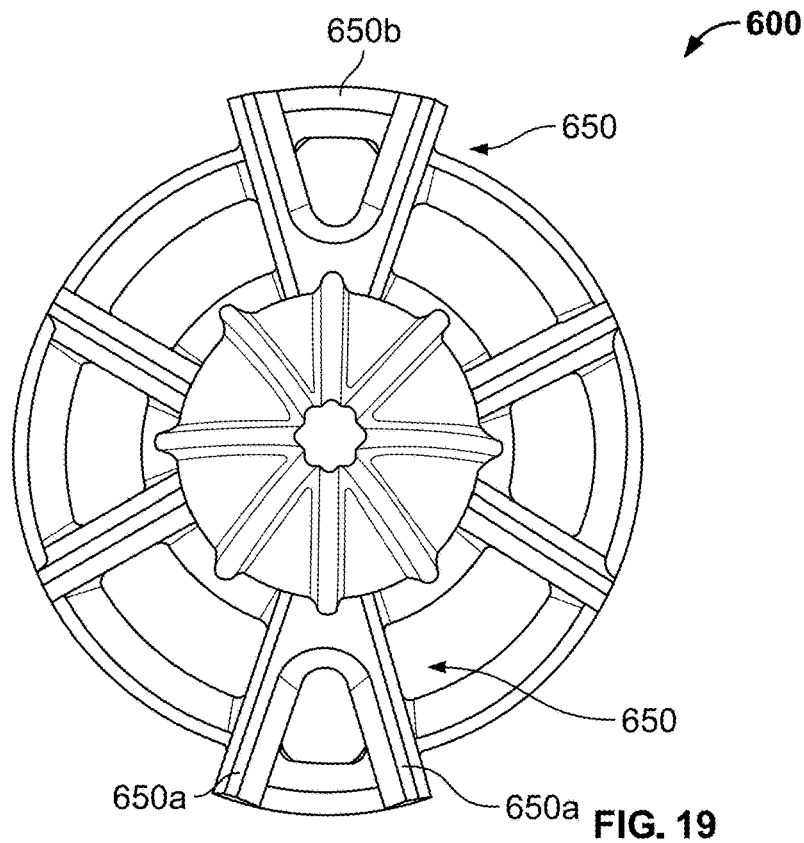
FIG. 19 is a top view of an alternate embodiment of the base of FIG. 17.

FIG. 19 shows base 600 substantially identical to base 500 except that extensions 650 include legs 650a and further include an outer leg 650b which extends in a direction substantially aligned with the outer perimeter of the collar. In the top view, extensions 650 each define an enclosed triangular shape in this example.

Figure 20:
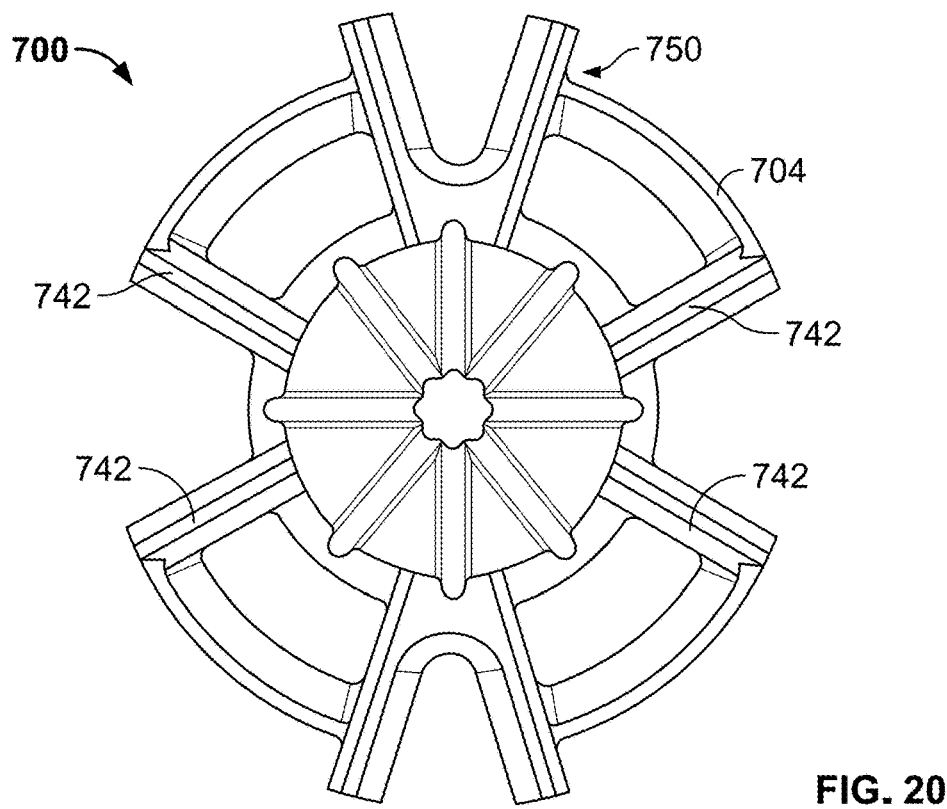
FIG. 20 is yet another alternative embodiment of the base of FIG. 17.

FIG. 20 shows base 700 substantially similar to base 500 in that extensions 750 define an open "V" shape rather than a closed shape as in FIG. 19. However, in this example, arms 742 define open "V" shapes, such that side wall 704 terminates at its connection with each of arms 742 so that the side wall 704 is discontinuous.

Figure 21:
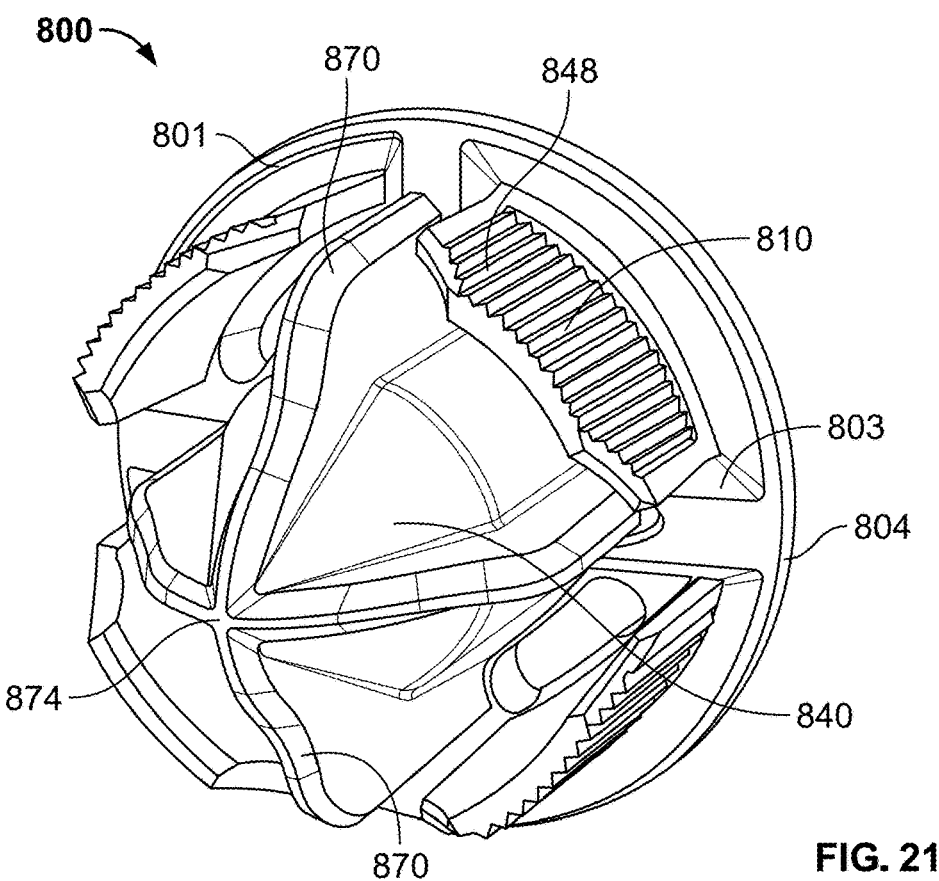
FIG. 21 is a top perspective view of a base of a stemless shoulder implant according to another aspect of the disclosure.
Figure 22:
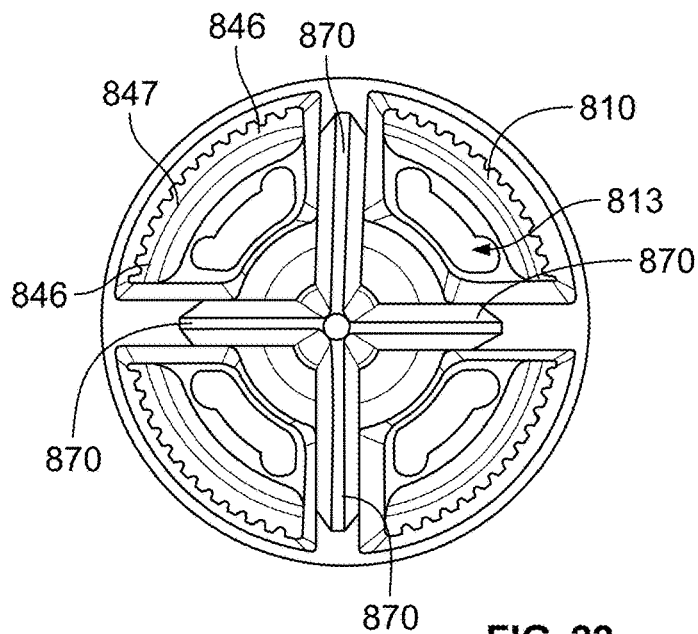
FIG. 22 is a top view of the base of FIG. 21.

FIGS. 21-22 show base 800 of a stemless implant according to another aspect of the present disclosure. In the illustrated embodiment, base 800 has a collar 801 that is generally annular, and may be circular, although in other examples, the base can be any shape, such as the above-described "shield" shape, triangular, trapezoidal, etc. Base 800 includes side wall 804 which extends between proximal surface (not shown) and bone-engaging surface 803. The proximal surface may include an opening (not shown) which is adapted to receive an articulating component (not shown) of the stemless implant, such as a prosthetic humeral head.

Base 800 includes central anchor 840 extending distally from bone-engaging surface 803 to second end 874. Anchor 840 includes a plurality of ribs 870, each rib projecting radially outward of distal end 874 and extending to bone-engaging surface 803.

Referring to FIG. 22, base 800 may include four ribs 870 that generally form a cross shape such that the ribs are about 90 degrees from adjacent ribs. However, it should be understood that other angles between the pairs of adjacent ribs may be suitable.

Base 800 includes keels 810 extending distally from bone-engaging surface 803 and positioned radially outward of anchor 840. Each keel 810 includes a central portion 847 positioned between two wings 846 which extend radially outward toward side surface 804. Outer surface 848 of keel 810 includes ridges extending in the direction of the longitudinal axis of base 800. Keels 810 may allow for initial fixation of the base within bone, with the ridges of outer surface 848 also allowing for frictional engagement and additional bone-ingrowth to achieve long term stability.

Base 800 includes continuous chisel slots 813 extending through bone-engaging surface 803 to proximal surface 802. In the illustrated embodiment, chisel slots 813 are positioned radially between anchor 840 and keels 810. Each chisel slot 813 may form a substantially "M" shape. With this positioning of chisel slots 813, a surgeon may insert a tool into each chisel slot 813 in order to chisel, ream, or otherwise cut away at bone that is adjacent to keels 810 and anchor 840. Additionally, the "M" shape of the chisel slots may provide more stability to a chisel tool as the shape of the chisel slot may require less bending of a correspondingly shaped tool.

Figure 23:
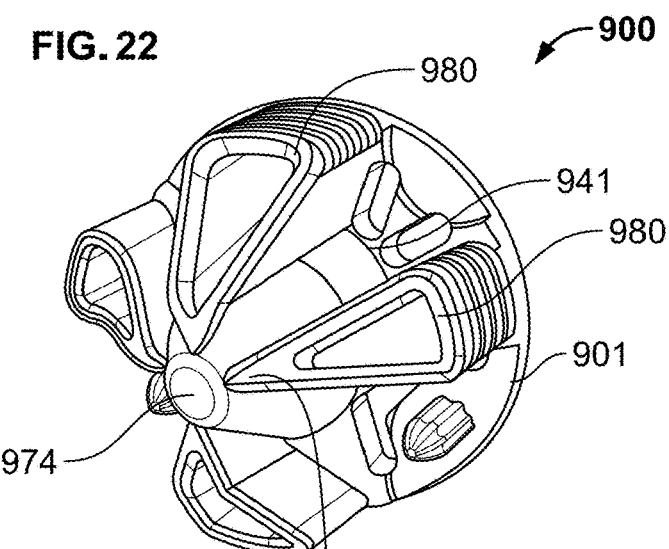
FIG. 23 is a top perspective view of a base of a stemless shoulder implant according to an aspect of the disclosure.
Figure 24:
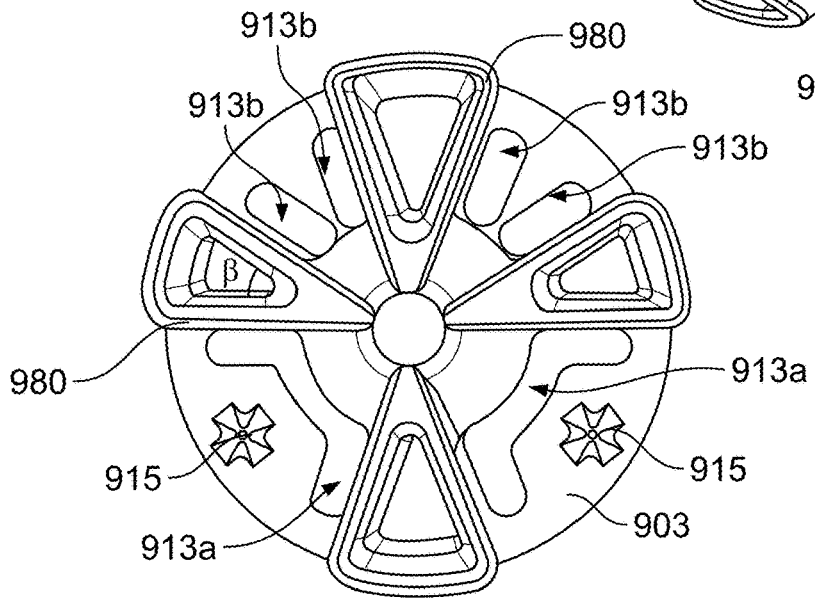
FIG. 24 is a top view of the base of FIG. 23.

Referring to FIGS. 23 and 24, base 900 is shown which includes certain similar features as base 800, described in connection with FIGS. 21 and 22 above. Base 900 includes collar 901 and anchor 940 extending distally from a first end 941 at collar 901 to a second end 974.

Base 900 further includes wings 980 extending radially outward from second end 974 of anchor 940 to bone-engaging surface 903 of collar 901. Wings 980 each extend to a position adjacent to or near side flange surface 904 of collar 901. In the illustrated embodiment, there are four wings 980. Adjacent wings 980 on the inferior portion of base 900 form an angle α therebetween, shown in FIG. 24. Adjacent wings 980 on the superior portion of base 900 form an angle β therebetween. Angle α and angle β may range from about 15 degrees to about 60 degrees. In the illustrated example, angle α is about 40 degrees and angle β is about 32 degrees. Accordingly, in the illustrated embodiment angle β is less than angle α, although in other embodiments the angles may be about equal.

The inferior portion of collar 901 further includes two "M" shaped chisel slots 913a and two peripheral anchors or pegs 915. Peripheral anchors 915 have a height that is less than a height of each of the central anchor 940 and the wings 980. Peripheral anchors 915 include flutes to enable engagement with bone such that the peripheral anchors are configured to facilitate initial fixation of base 900 upon implantation in bone. Between adjacent wings 980 is a respective one of the "M" shaped chisel slots 913a and a peripheral anchor 915 positioned radially outward of the chisel slot 913a.

The superior portion of collar 901 further includes two oblong chisel slots 913b between adjacent wings 980. Base 900 is asymmetrical about the medial-lateral direction, or about a horizontal line in FIG. 24. In other words, the superior and inferior portions are asymmetric from one another. This asymmetry allows for rotational alignment or clocking of instruments relative to the base, as instruments are coupled to the base relative to a superior direction. Thus, the asymmetry prevents inaccurate assembly.

Figure 25:
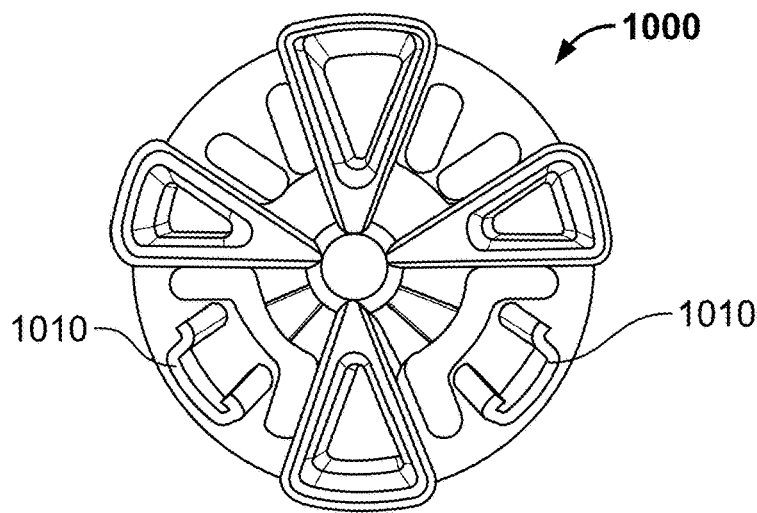
FIG. 25 is a top view of a base of a stemless shoulder implant according to another aspect of the present disclosure.

FIG. 25 shows base 1000 substantially similar to base 900, except that base 1000 includes keels 1010, rather than peripheral anchors 915.

Figure 26:
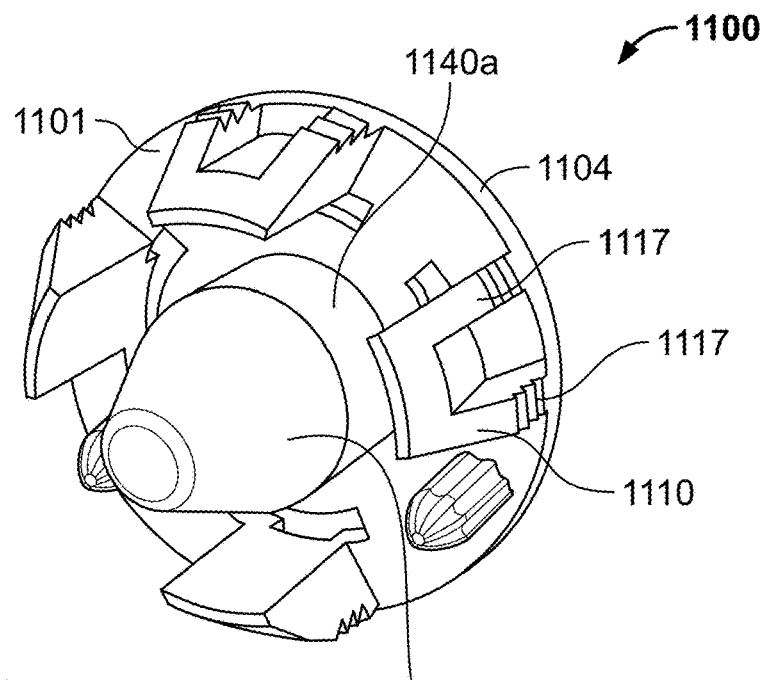
FIG. 26 is a top perspective view of a base of a stemless shoulder implant according to another aspect of the disclosure.
Figure 27:
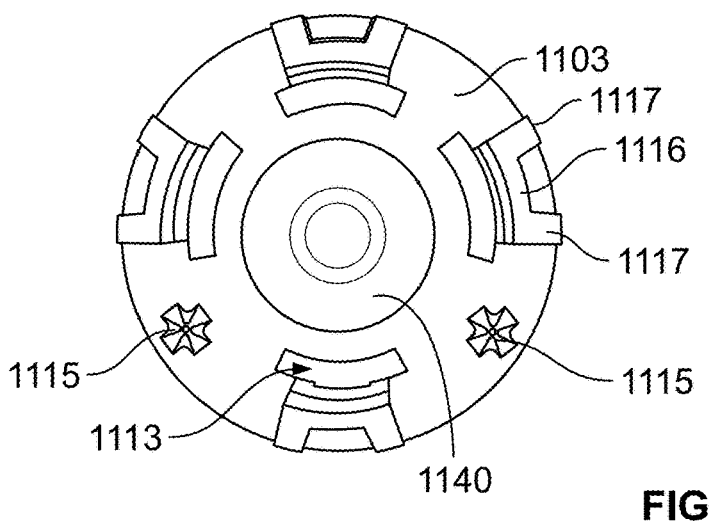
FIG. 27 is a top view of the base of FIG. 26.

Referring to FIGS. 26-27, base 1100 of a stemless shoulder implant system is shown according to another aspect of the present disclosure. Base 1100 includes collar 1101 and anchor 1140 extending distally from bone-engaging surface 1103 of collar 1001. Anchor 1140 includes a substantially cylindrical proximal portion 1140a and an inwardly tapering distal portion 1140b.

Collar 1101 includes keels 1110 positioned radially outward of anchor 1140. Keels 1110 each include a central portion 1116 and two arms 1117 at opposing ends of the central portion and extending radially outward of the central portion such that the keel, from the top view, has a substantially "U" profile. Arms 1117 each include ridges or steps on at least a portion of the arm to allow bone ingrowth and to provide additional frictional engagement with the bone. An elongated chisel slot 1113 is positioned adjacent each keel 1110 between the keel and anchor 1140 to facilitate removal of bone engaged with the keels during a revision surgery to more effectively loosen the base from bone.

The inferior portion of collar 1101 includes peripheral anchors 1115, identical to peripheral anchors 915. In this embodiment, peripheral anchors 1115 have a first height less than a second height of the keels, both the first and the second heights being less than a height of the central anchor 1140.

Figure 28:
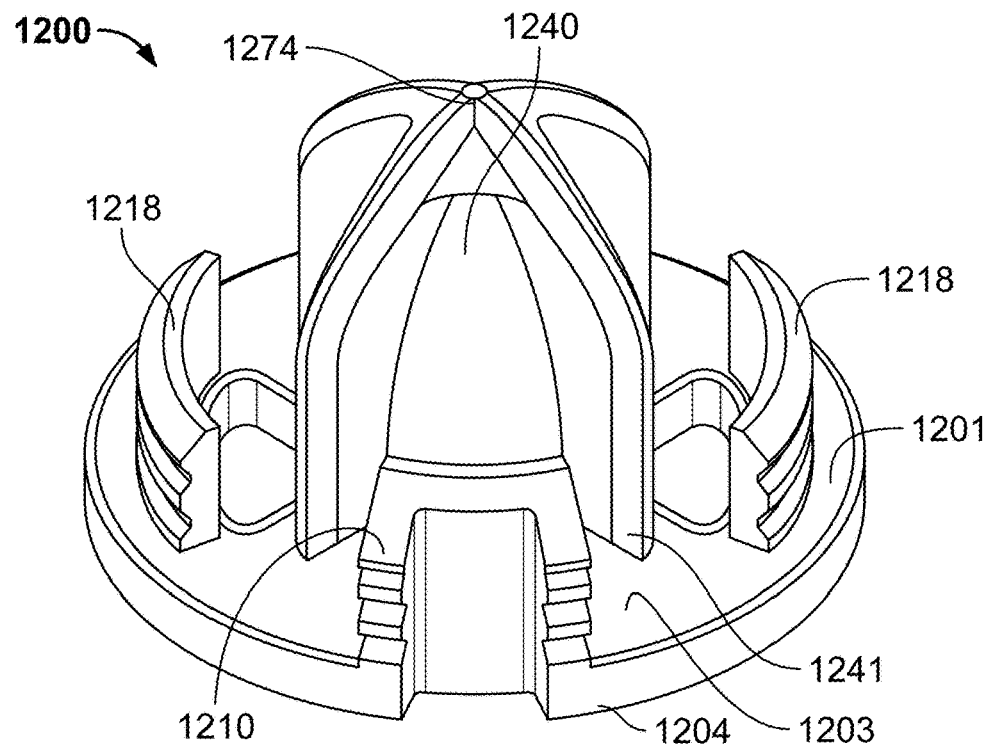
FIG. 28 is a side perspective view of a base of a stemless shoulder implant according to another aspect of the disclosure.
Figure 29:
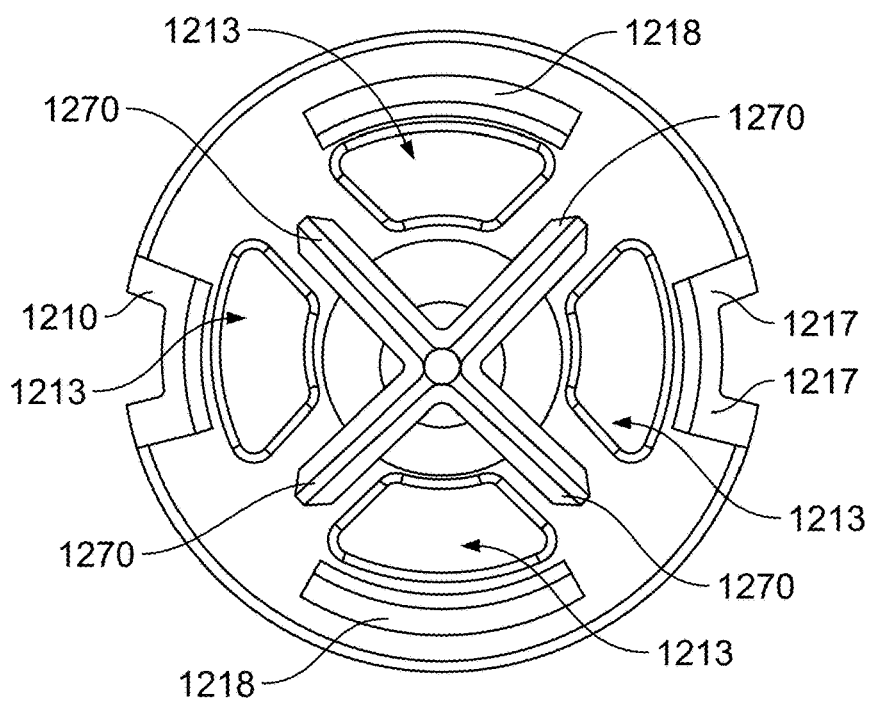
FIG. 29 is a top view of the base of FIG. 28.

Referring to FIGS. 28 and 29, a base 1200 of a stemless shoulder implant according to another aspect of the present disclosure is shown. Base 1200 includes anchor 1240 extending distally from collar 1201. In this embodiment, anchor 1240 includes four ribs 1270 extending outwardly from first end 1241 of anchor 1240 to second end 1274 of anchor 1240. Ribs 1270 are spaced apart from one another at about 90 degrees. Base 1200 further includes two keels or extensions 1218 positioned on opposing superior and inferior sides of anchor 1240 and extending distally from bone-engaging surface 1203. Extensions 1218 have a generally inwardly-facing concave shape. Base 1200 further includes keels 1210 positioned on opposing anterior and posterior sides of anchor 1240. Keels 1210 may be identical to keels 1110 of base 1100, described in connection with FIGS. 26 and 27, except that keel arms 1217 connect to and intersect with side flange surface 1204 of collar 1201. In this manner, the outer perimeter of collar 1201 is interrupted by keels 1210.

As shown in FIG. 29, base 1200 includes chisel slots 1213 positioned between anchor 1240 and each of the extensions 1218 and the keels 1210. Accordingly, in the illustrated embodiment, there are four chisel slots 1213. Further, each chisel slot 1213 has a substantially trapezoidal shape.

In an alternative embodiment, the bases described above may include anchors that are externally threaded rather than including ribs. The external threads compress the bone while having the threaded connection with the bone.

Further, in another alternative embodiment, the keels described in connection with bases 810, 1010, 1110 and 1210 may have a helical shape such that the keel rotates under impaction. In this example, the base may be inserted in two steps with impaction and then rotation to achieve final seating of the base.

Figure 30:
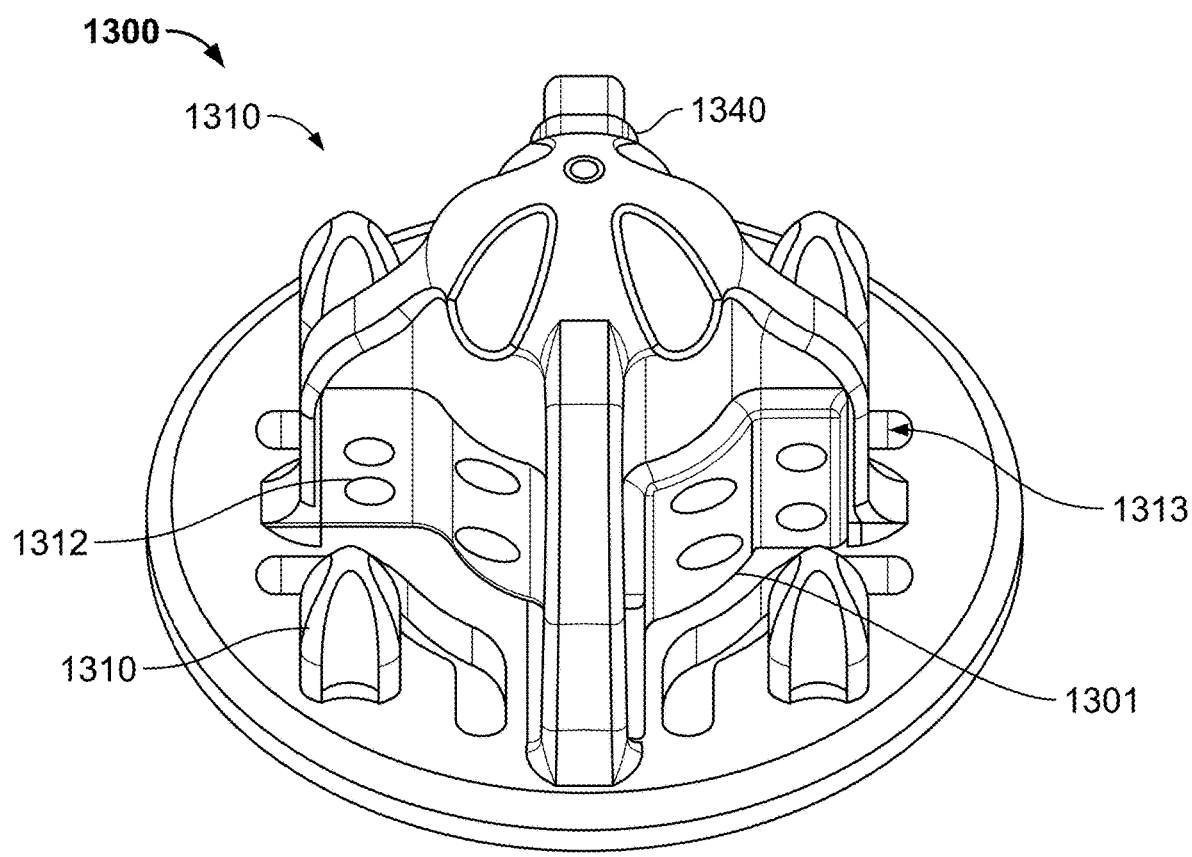
FIG. 30 is a side perspective view of a base of a stemless shoulder implant according to another aspect of the present disclosure.

FIG. 30 shows base 1300 according to another embodiment of the present disclosure. Base 1300 includes collar 1301 and anchor 1340 extending distally from the collar. Base 1300 further includes a plurality of peripheral pegs 1310 for providing initial fixation of the base within the bone. Collar 1301 defines chisel slots 1313 positioned between each peg 1310 and anchor 1340 which facilitate removal of the bone around the anchor and the peripheral pegs to allow for a revision surgery.

Anchor 1340 includes a reduced press-fit region adjacent its connection to collar 1301, which includes a plurality of shallow cavities or dimples 1312 around the circumference of the anchor. In the illustrated embodiment, dimples 1312 are spaced apart around the circumference. Dimples 1312 generate a force component that works into the bone to provide greater stability of the base 1300.

Figure 31:
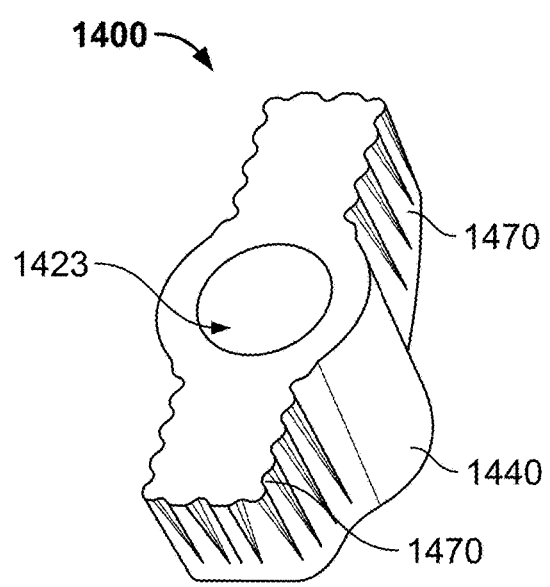
FIG. 31 is a bottom perspective view of a base of a stemless shoulder implant according to another aspect of the present disclosure.
Figure 32:
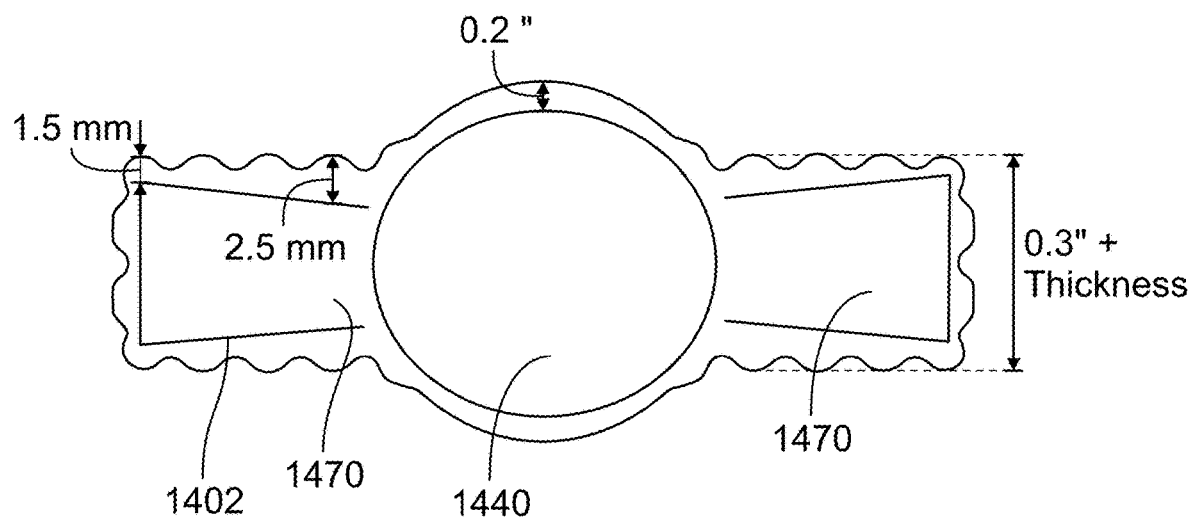
FIG. 32 is a top view of the base of FIG. 31.
Figure 33:
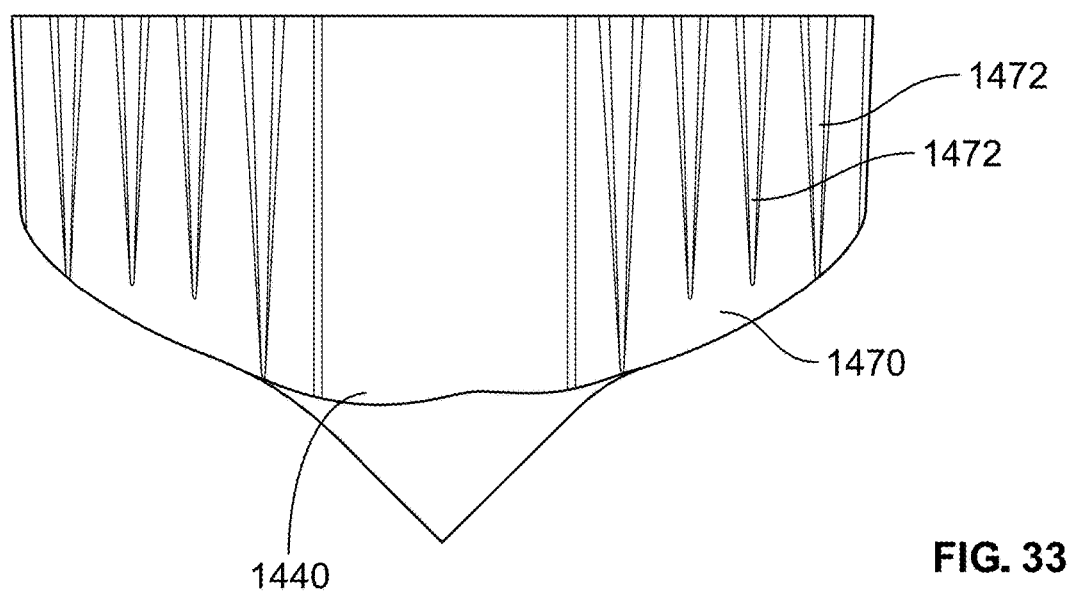
FIG. 33 is a side view of the base of FIG. 31.

FIGS. 31-33 show base 1400 according to another embodiment of the present disclosure. Base 1400 is adapted to receive an articulating component (not shown) of the stemless implant. In the illustrated example, base 1400 may be adapted to couple to a proximal humerus of a patient, with a prosthetic humeral head adapted to couple to the base. In this regard, base 1400 includes opening 1423 extending distally into the base for receiving at least a portion of the prosthetic humeral head. The prosthetic humeral head is intended to articulate with a native or prosthetic glenoid of the shoulder joint. The opening may have any shape that suitably mates with the corresponding portion of the prosthetic humeral head, in one example a taper such as a Morse taper may be used to lock the prosthetic humeral head to base 1400.

Base 1400 is designed to increase the press fit between the base and the bone at areas of the bone having lower density. This provides equal stability along the base and allows for an easier revision surgery. The schematic corresponding cavity created in the bone for the implant is shown as line 1402 in FIG. 32. The cavity is created such that the press-fit is greatest at the connection of the ribs 1470 to the anchor 1440. As shown, the press-fit is greater toward the center of the ribs 1470, e.g. about 2.5 mm near anchor 1440, as compared to the side periphery, e.g. about 1.5 mm at the corner. Further the press-fit with the cavity at the center or anchor 1440 is about 0.2 inches. Base 1400 further includes anchor 1440 and ribs 1470 extending in opposite directions from the anchor, which in the illustrated embodiment there are two ribs 1470 extending in the medial-lateral direction. Ribs 1470 include vertical fins 1472 for additional fixation, although in other examples the fixation feature may include horizontal barbs.

Figure 34:
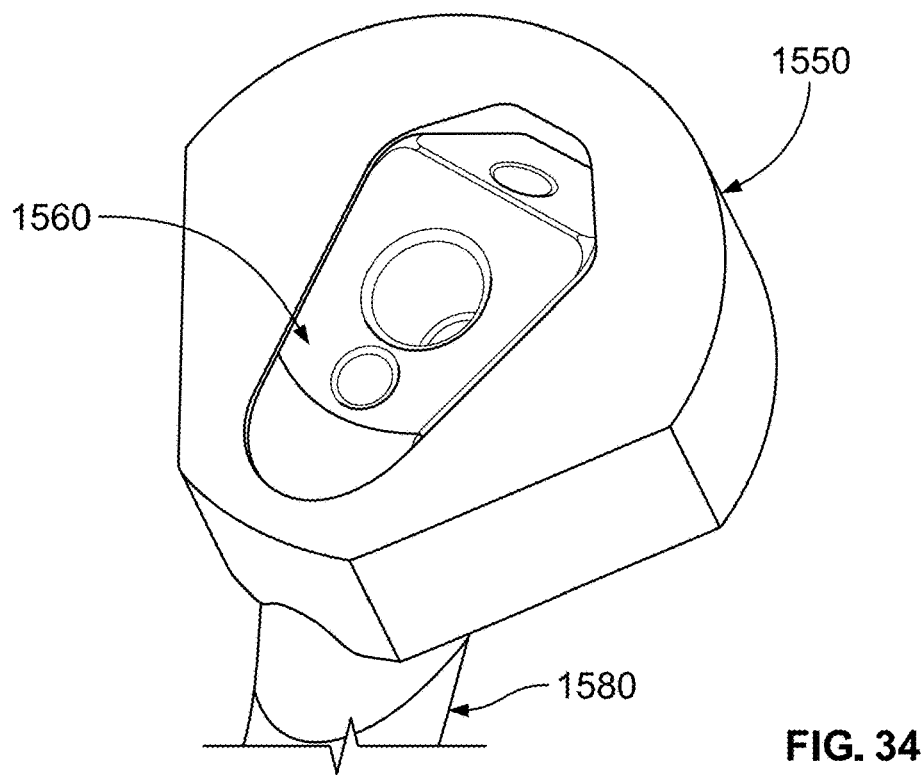
FIG. 34 is a side perspective view of an adaptor in conjunction with a stemmed implant according to another aspect of the present disclosure.
Figure 35:
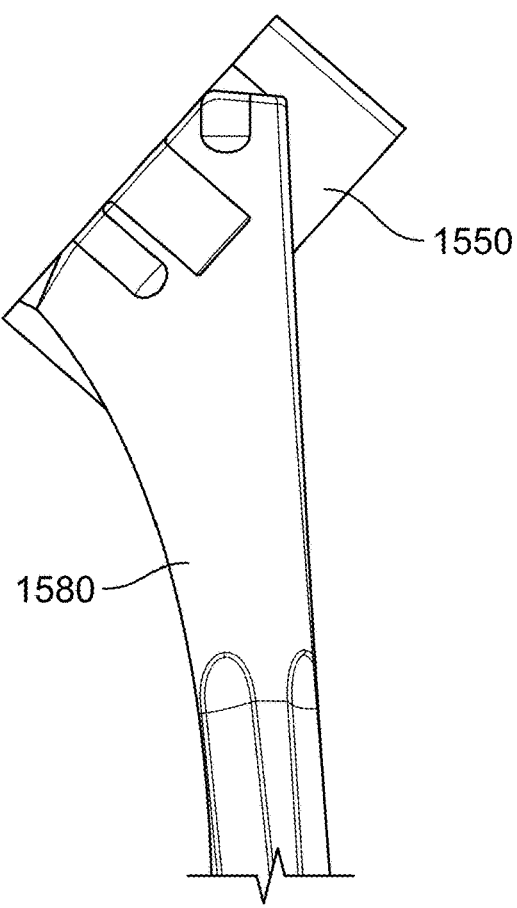
FIG. 35 is a side view of the adaptor and stemmed implant of FIG. 34.

FIGS. 34 and 35 show adaptor 1550 according to another embodiment of the present disclosure. Adaptor 1550 is designed for use with a revision surgery of a previously-implanted stemless base component. During the revision surgery, the previously-implanted stemless base component is explanted, which results in a cavity may result in a proximal portion of the humeral bone. The stemless base component is explanted in a manner to save as much bone as possible, and thus the cavity generally has a shape that is similar to the base component that is removed. Thus, during a revision of a base component such as base 100, or other similarly shaped base components described herein, the resulting cavity has a generally "shield" shape that is similar to the "shield" shape of the removed base component. During the implantation of the subsequent stemless implant, such as a stemmed implant, it is advantageous to fill some of the cavity. Therefore, an adaptor that fills some or all of the cavity is advantageous when used in conjunction with a stemmed implant. For example, adaptor 1550 is implanted along with stem 1580, with stem 1580 designed to stabilize the bone.

Adaptor 1550 is designed to match the "shield" shape of base 100, or the other "shield" shape bases described above, with the superior portion defining an arc shape and the inferior portion defining a substantially triangular shape. With the shape of the adaptor substantially similar to the shape of the previously-implanted, and subsequently removed, base component allows the adaptor to fill the void space in the bone. Adaptor 1550 includes opening 1560 for receiving a proximal portion of stem 1580. Adaptor 1550 may include porous portions, such as on the on the periphery, for additional fixation.

Stem 1580 is coupled to adaptor 1550 with cement or is sized for a press-fit connection. Stem 1580 may be a standard stemmed implant which is known in the art and is adapted to receive a proximal head component. Adaptor 1550 thus facilitates a revision stemless surgery of base 100 to a stemmed implant with increased stability and fixation.

Although described with reference to certain embodiments above, each of the bases described herein may include portions of enhanced fixation surfaces, including Tritanium® by Howmedica Osteonics Corporation. Such enhanced fixation surfaces are generally porous and may be positioned on bone-engaging surface and/or a portion of anchor to facilitate bone ingrowth. Other coatings may be used in addition to the enhanced fixation surface to provide additional fixation benefits. Further, each of the bases described herein can define the "shield" shape to allow for increased stability and fixation.

Still further, each of the bases described herein may be produced through additive layer manufacturing (ALM), e.g. 3D printing. In some examples, ALM processes are powder-bed based and involve one or more of selective laser sintering (SLS), selective laser melting (SLM), and electron beam melting (EBM), as disclosed in U.S. Pat. Nos. 7,537,664; 8,728,387; 9,180,010; and 9,456,901, the disclosures of which are hereby incorporated by reference in their entireties herein.

In some arrangements, the base is formed using an ALM fabrication process, such as SLS, SLM or EBM described above, fused deposition modeling (FDM), or other appropriate 3D printing technologies known to those skilled in the art. When employing powder-bed based technologies, articles are produced in layer-wise fashion according to a predetermined digital model of such articles by heating, e.g., using a laser or an electron beam, multiple layers of powder, which preferably may be a metallic powder, that are dispensed one layer at a time. The powder is sintered in the case of SLS technology and melted in the case of SLM technology, by the application of laser energy that is directed in raster-scan fashion to portions of the powder layer corresponding to a cross section of the article. After the sintering or melting of the powder on one particular layer, an additional layer of powder is dispensed, and the process repeated, with sintering or melting taking place between the current layer and the previously laid layers until the article is complete. The powder layers similarly may be heated with EBM technology. Additive manufacturing techniques such as the ALM processes described above may be employed to form the implant including the porous layers. In some instances, materials for one layer may be different than the materials for successive layers.

To form the porous layer in particular, porous geometries may be digitally modeled using cells as described in U.S. Pat. Nos. 9,180,010 and 9,135,374, the disclosures of which are hereby incorporated by reference in their entireties herein. The model may be manipulated to build a patient specific implant, and such manipulations may be based on a CT scan and/or an MRI.

During printing, a first layer or portion of a layer of powder is deposited and then scanned with a high energy beam to create a portion of a plurality of predetermined porous geometries. Successive layers of powder are then deposited onto previous layers of the powder and then scanned with the high energy beam. The scanning and depositing of successive layers of the powder continues the building process of the predetermined porous geometries. The porous geometries of the formed porous layers may define pores that may be interconnecting to provide an interconnected porosity. Further details regarding this high energy beam ALM process are described in U.S. Prov. Pat. App. No. 62/517,456, hereby incorporated by reference herein in its entirety.

Materials used to form the devices described above with an ALM process include, but are not limited to, metals (e.g., metal powder) that may be any one or any combination of titanium and its alloys (such as a porous titanium alloy, including Tritanium® by Howmedica Osteonics Corporation), stainless steel, magnesium and its alloys, cobalt and its alloys including cobalt chromium alloys, nickel and its alloys, platinum, silver, tantalum niobium, and other super elastic materials such as copper-aluminum alloys. Non-metallic materials may also be used and include, but are not limited to, implantable plastics. These may be any one of or a combination of wax, polyethylene (PE) and variations thereof, polyetheretherketone (PEEK), polyetherketone (PEK), acrylonitrile butadiene styrene (ABS), silicone, and cross-linked polymers, bioabsorbable glass, ceramics, and biological active materials such as collagen/cell matrices.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A base member of a stemless shoulder implant, the base member comprising:
a proximal collar having a proximal surface and a bone-engaging surface opposite the proximal surface with a side wall extending therebetween, the proximal surface having a superior portion and an inferior portion, the superior portion defining an arc shape and the inferior portion defining a substantially triangular shape tapering from the superior portion to an apex, the superior portion and the inferior portion defining a perimeter of the proximal collar, the bone-engaging surface including a porous surface configured to allow bone ingrowth into the base member; and a plurality of peripheral supports positioned radially outwardly of a longitudinal axis of the base member and extending distally from the side wall, the plurality of peripheral supports including a first peripheral support extending distally from the apex of the inferior portion, at least one peripheral support defining a concave inner surface configured to enhance fixation of the base member to a bone.

2. The base member of claim 1, further comprising a central anchor extending distally along the longitudinal axis of the base member from the bone-engaging surface of the collar a first distance to a central tip.

3. The base member of claim 2, wherein the central anchor includes a plurality of ribs extending radially outward of the central anchor.

4. The base member of claim 2, further comprising at least one chisel slot extending from the bone-engaging surface to the proximal surface adjacent a portion of the central anchor, the at least one chisel slot configured to receive a tool for removing bone.

5. The base member of claim 2, wherein each peripheral support extends a second distance to a peripheral tip, the first distance being greater than the second distance.

6. The base member of claim 3, wherein each of the plurality of ribs extends along the central anchor and connects to a respective one of the plurality of peripheral supports.

7. The base member of claim 6, wherein each of the plurality of ribs connects to an inner surface of the respective one of the peripheral supports.

8. The base member of claim 1, wherein the arc of the superior portion extends between a second peripheral support and a third peripheral support of the plurality of peripheral supports.

9. The base member of claim 2, wherein the base member includes four peripheral supports.

10. The base member of claim 9, further comprising at least one chisel slot extending from the bone-engaging surface to the proximal surface adjacent a portion of the central anchor, the at least one chisel slot configured to receive a tool for removing bone.

11. The base member of claim 10, wherein the base member includes four chisel slots.

12. The base member of claim 1, wherein the triangular shape of the inferior portion is defined by a first side edge extending along a first line and a second side edge extending along a second line, an angle defined between the first line and the second line being from about 60 degrees to about 75 degrees.

13. The base member of claim 2, wherein an angle from the central tip of the central anchor to opposing side walls of a respective one of the plurality of peripheral supports is about 30 degrees.

14. The base member of claim 1, wherein each of the plurality of peripheral supports extends along the same diameter of the base member such that each support is an equal distance from the longitudinal axis of the base.

15. The base member of claim 8, wherein an angle between a first central point of the first peripheral support and a second central point of the second peripheral support is from about 105 degrees to about 120 degrees.

16. The base member of claim 7, wherein a peripheral tip of each of the peripheral supports defines a free end, and the plurality of ribs connect to a respect one of the peripheral supports proximal to the peripheral tip thereof.

17. The base member of claim 2, wherein a central axis of the central anchor is coaxial with the longitudinal axis and perpendicular to the proximal surface of the proximal collar.

18. The base member of claim 17, wherein the peripheral supports are parallel to the central axis of the central anchor.

19. The base member of claim 1, wherein the arc shape of the superior portion defines a diameter of the proximal collar, and the apex of the triangular shape of the inferior portion lies on the diameter formed by the arc shape of the superior portion.

20. The base member of claim 1, wherein the porous surface includes a porous titanium alloy.

21. A base member of a stemless shoulder implant, the base member comprising:

a proximal collar having a proximal surface and a bone-engaging surface opposite the proximal surface with a side wall extending therebetween, the proximal surface having a superior portion and an inferior portion, the superior portion defining an arc shape and the inferior portion defining a substantially triangular shape tapering from the superior portion to an apex, the superior portion and the inferior portion defining a perimeter of the proximal collar; and a plurality of peripheral supports positioned radially outwardly of a longitudinal axis of the base member and extending distally from the side wall, the plurality of peripheral supports including a first peripheral support extending distally from the apex of the inferior portion, at least one peripheral support defining a concave inner surface and an outer surface with grooves, the grooves including a porous material configured to enhance fixation of the base member to a bone.

* * * * *